(12) United States Patent
Hodgson et al.

(10) Patent No.: US 11,720,809 B2
(45) Date of Patent: Aug. 8, 2023

(54) MODELING FOR COMPLEX OUTCOMES USING CLUSTERING AND MACHINE LEARNING ALGORITHMS

(71) Applicant: The Ronin Project, Inc., San Mateo, CA (US)

(72) Inventors: Dave Hodgson, San Mateo, CA (US); Brian Chhor, San Mateo, CA (US); Jérémie Meyer de Ville, San Mateo, CA (US); Michael Elashoff, San Mateo, CA (US); Christine Swisher, San Mateo, CA (US)

(73) Assignee: THE RONIN PROJECT, INC., San Mateo, CA (US)

( * ) Notice: Subject to any disclaimer, the term of this patent is extended or adjusted under 35 U.S.C. 154(b) by 0 days.

(21) Appl. No.: 16/893,333

(22) Filed: Jun. 4, 2020

(65) Prior Publication Data

US 2020/0387810 A1 Dec. 10, 2020

Related U.S. Application Data

(60) Provisional application No. 62/857,721, filed on Jun. 5, 2019.

(51) Int. Cl.
*G06N 5/04* (2006.01)
*G06N 20/00* (2019.01)

(52) U.S. Cl.
CPC ............... *G06N 5/04* (2013.01); *G06N 20/00* (2019.01)

(58) Field of Classification Search
CPC ................................ G06N 5/04; G06N 20/00
See application file for complete search history.

(56) References Cited

U.S. PATENT DOCUMENTS

| | | | |
|---|---|---|---|
| 10,318,503 B1 | 6/2019 | Swamy | |
| 2007/0118399 A1 | 5/2007 | Avinash et al. | |
| 2010/0174670 A1 | 7/2010 | Malik et al. | |
| 2014/0006013 A1 | 1/2014 | Markatou et al. | |
| 2014/0046683 A1 | 2/2014 | Michelson et al. | |
| 2014/0100866 A1 | 4/2014 | Wilkerson et al. | |
| 2014/0143251 A1 | 5/2014 | Wang et al. | |
| 2016/0063097 A1 | 3/2016 | Brown et al. | |
| 2016/0117589 A1 | 4/2016 | Scholtes | |
| 2016/0326586 A1* | 11/2016 | Scherer | G16B 30/00 |
| 2017/0140114 A1* | 5/2017 | Are | G06N 20/00 |
| 2017/0173110 A1* | 6/2017 | Ko | A61K 31/555 |
| 2017/0228661 A1 | 8/2017 | Chien et al. | |

(Continued)

OTHER PUBLICATIONS

Oftadeh, Elaheh. Complex Modelling of Multi-Outcome Data with Applications to Cancer Biology. Diss. University of Kent,, 2017. (Year: 2017).*

(Continued)

*Primary Examiner* — Kevin W Figueroa
(74) *Attorney, Agent, or Firm* — Wilson Sonsini Goodrich & Rosati

(57) ABSTRACT

Described herein are systems and methods for modeling complex outcomes using clustering and machine learning algorithms. Machine learning algorithms and models can be implemented on platforms comprising one or more user interfaces and an insight engine. In these embodiments, insight engine comprises a machine learning software algorithm (or module) configured to ingest data and generate insights.

30 Claims, 15 Drawing Sheets

(56) References Cited

U.S. PATENT DOCUMENTS

| | | | |
|---|---|---|---|
| 2019/0114556 A1* | 4/2019 | Ye | G06N 20/00 |
| 2019/0371443 A1* | 12/2019 | Petricoin, III | G16H 20/10 |
| 2019/0371475 A1* | 12/2019 | Oliveira | G16H 10/60 |
| 2020/0143291 A1 | 5/2020 | Besanson Tuma et al. | |
| 2020/0143922 A1* | 5/2020 | Chekroud | G06K 9/6218 |
| 2020/0194131 A1* | 6/2020 | Stevens | G06K 9/00483 |

OTHER PUBLICATIONS

PCT/US2020/036148 International Search Report and Written Opinion dated Aug. 18, 2020.

* cited by examiner

MODELING FOR COMPLEX OUTCOMES USING CLUSTERING AND MACHINE LEARNING ALGORITHMS

CROSS-REFERENCE

This application claims the benefit of U.S. Provisional Patent Application No. 62/857,721 filed on Jun. 5, 2019, which is incorporated by reference in its entirety.

BACKGROUND

Given, in part at least, the breadth of medical information now widely available along with the rapid rate at which new medical information is discovered (through, e.g., new studies) as well as the rate of development of new therapies, providing effective healthcare to patients has become difficult for today's healthcare providers. Current methods for modeling this information fail to effectively process and evaluate large and complex data sets for various diseases.

Cancer in particular has long been and remains a disease that is difficult to treat given, among other things, the complexity of the disease process, the differences between cancer types, and the differences between patients. In addition, while promising therapeutics and therapeutic regimens are being constantly formulated and developed, delivering the right therapeutic and/or therapeutic regimen to a patient is a complicated process for the health care provider.

SUMMARY

Described herein are systems and methods utilizing machine learning algorithms for enhanced data processing and analysis. In some embodiments, machine learning algorithms and models process medical data such as electronic medical records, laboratory results, medical imaging, and other relevant medical information to identify clusters of data points based on multi-dimensional parameters. These clusters can form the basis for multi-outcome based predictive models which can be integrated into a data insights engine to generate analytic insights to inform the decision-making process. Single-outcome predictive models can also be generated and used to generate additional analytic insights.

Described herein is a computer-implemented system for multi-outcome modeling and input categorization using machine learning, the system comprising: (a) a processor; (b) a non-transitory computer readable storage medium encoded with a computer program that causes the processor to: (i) receive outcome data comprising a plurality of outcome categories for a plurality of subjects; (ii) process said outcome data to generate a plurality of data points corresponding to said plurality of subjects; (iii) compute distances between each of said plurality of data points based on said plurality of outcome categories, thereby generating a distance matrix; (iv) set each of said plurality of data points as a cluster, thereby providing a plurality of clusters corresponding to said plurality of data points; (v) identify two clusters that are closest within said plurality of clusters using said distance matrix and merge said two clusters that are closest into a single cluster; (vi) update said distance matrix by replacing said two clusters that are closest with said single cluster; (vii) repeat steps v)-vi) until a hierarchical relationship between each of said plurality of data points has been established, wherein said hierarchical relationship comprises two or more clusters defined by said plurality of outcome categories; and (viii) obtain a data set for said plurality of subjects; (ix) extract features from said data set using a natural language processing algorithm to generate a standardized data set; (x) label said standardized data set with said plurality of outcome categories defining said two or more clusters; and (xi) generate a cluster prediction classifier configured to categorize an input into at least one of said two or more clusters defined by said plurality of outcome categories, wherein said classifier is modeled with a machine learning algorithm using said standardized data set labeled with said plurality of outcome categories defining said two or more clusters. In some embodiments, said one or more processors are further caused to generate a dendrogram visually representing said hierarchical relationship between each of said plurality of data points. In some embodiments, said one or more processors are further caused to generate an insight through a user interface, wherein said insight is based on a classification of said input into at least one of said two or more clusters. In some embodiments, said plurality of data points comprises binary values, nominal values, ordinal values, text or string values, quantitative values, or any combination thereof. In some embodiments, said distances are computed using simple matching distance, Jaccard's distance, Hamming distance, normalized rank transformation, Spearman distance, footrule distance, Kendall distance, Cayley distance, Ulam distance, Euclidean distance, City block distance, Chebyshev distance, Minkowski distance, Canberra distance, Bray Curtis distance, angular separation, or correlation coefficient.

Described herein is a computer-implemented method for multi-outcome modeling using machine learning comprising: (a) receiving a data set comprising outcome information corresponding to a plurality of patients; (b) applying a clustering algorithm to said outcome information to identify two or more clusters, wherein each of said two or more clusters is defined by a plurality of outcomes; (c) generating a multi-outcome predictive model using a machine learning algorithm, wherein said multi-outcome predictive model is trained using said data set and said plurality of outcomes defining each of said two or more clusters such that said machine learning algorithm determines associations between a plurality of features within said data set and said plurality of outcomes; and (d) evaluating an input data for a patient using said multi-outcome predictive model to generate an output comprising a determination of a cluster selected from said two or more clusters, wherein said patient is predicted to have at least one outcome of said plurality of outcomes. In some embodiments, the method further comprises converting said data set into a plurality of data points, each of said plurality of data points comprising parameters corresponding to said outcome information. In some embodiments, the method further comprises computing distances between each of said plurality of data points based on said parameters, thereby generating a distance matrix. In some embodiments, the method further comprises generating a dendrogram visually representing said two or more clusters. In some embodiments, said clustering algorithm comprises K-means clustering, mean-shift clustering, or hierarchical clustering. In some embodiments, said clustering algorithm is a hierarchical clustering algorithm. In some embodiments, said multi-outcome predictive model comprises random forest, gradient boosted trees, or penalized multinomial regression. In some embodiments, said data set comprises health data for said plurality of subjects retrieved from an electronic medical record. In some embodiments, the method further comprises processing said electronic medical record using a natural language processing algorithm to extract a plurality of features from said data set for training said multi-outcome predictive model. In some embodiments, said natural language processing algorithm comprises one or more rules for keyword identification, unit conversion, internal consistency, or any combination thereof. In some embodiments, said natural language processing algorithm comprises a natural language processing model configured to annotate said electronic medical record with gold standard labels. In some embodiments, said natural language processing algorithm comprises generating rules based on raw data from the electronic medical record, and then using the rules to train a model to apply to said raw data to standardize said electronic medical record. In some embodiments, the method further comprises generating one or more insights to assist in providing guidance for a treatment, wherein said one or more insights is based on said output comprising said determination of said cluster selected from said two or more clusters. In some embodiments, the method further comprises providing a healthcare provider application comprising a healthcare provider interface configured to present a healthcare provider with said one or more insights comprising said guidance regarding said treatment and a patient application comprising a patient interface configured to receive said input data for said patient. In some embodiments, said healthcare provider interface comprises a first plurality of portals, wherein at least one of said first plurality of portals comprises a patient context data grouping comprising said health data. In some embodiments, at least one of said first plurality of portals comprises an outcomes navigator data grouping comprising said outcome information. In some embodiments, said patient context grouping comprises a second plurality of portals comprising an interactive timeline of a disease of said patient, interactive radiology imaging of said patient, a medical history of said patient and a current status of said patient, or any combination thereof. In some embodiments, said two or more clusters are based on outcome information comprising one or more of progression, adverse event status, treatment status, or mortality. In some embodiments, said multi-outcome predictive model comprises a plurality of features comprising one or more of: (1) age, (2) gender, (3) race, (4) exposure, (5) co-morbidity, (6) diagnosis, (7) prognosis, (8) tumor pathology, (9) serum markers, (10) radiology findings, (11) family history, (12) surgical history, (13) treatment plan, (14) treatment regimen, or (15) treatment goal. In some embodiments, the method further comprises selecting published data that is most relevant to said patient and presenting said published data within said healthcare provider interface, wherein at least one of said second plurality of portals is configured to present published data relating to said patient. In some embodiments, at least one of said second plurality of portals comprises a comparison of a performance of said healthcare provider to a performance of other healthcare providers. In some embodiments, said plurality of outcomes comprises cancer survival cancer progression, adverse event for a treatment, or any combination thereof. In some embodiments, said adverse event comprises neutropenia, leucopenia, thrombocytopenia, fatigue, pain, mucositis, skin rash, nausea, vomiting, constipation, diarrhea, cognitive dysfunction, nerve damage, appetite loss, organ damage, or any combination thereof. In some embodiments, the method further comprises generating one or more single-outcome predictive models using a machine learning algorithm, and evaluating said input data for said patient using said one or more single-outcome predictive models to generate an output comprising one or more predicted outcomes. In some embodiments, said one or more single-outcome predictive model comprise random forest, gradient boosted trees, penalized linear regression, penalized logistic regression, cox regression, or recurrent neural network.

Described herein are platforms and methods for treating a patient. In some embodiments of the platforms and methods described herein, a platform and method comprises one or more user interfaces and a data insights engine. In these embodiments, the platform and method comprises a data insights engine which comprises a machine learning software algorithm (or module) configured to ingest patient data and generate insights relating to patient care. In some embodiments of the platforms and methods described herein, the platforms and methods comprise custom user interfaces that comprise a healthcare provider interface and a patient interface. In some embodiments, the platforms and methods further comprise a third party interface.

Described herein is a platform configured to assist a healthcare provider in the provision of a treatment to a patient, the platform comprising:
  (a) a healthcare provider application comprising a healthcare provider interface configured to present the healthcare provider with guidance regarding the treatment;
  (b) a patient application comprising a patient interface configured to receive patient input from the patient; and
  (c) a server processor configured to provide a data insights engine comprising:
    (i) an ingestion module for receiving:
      (1) health data of the patient;
      (2) outcome data comprising an outcome of a similarly situated patient; and
      (3) the patient input;
    (ii) an analysis module for determining a patient related insight based on the health data, the outcome data, and the patient input; and
    (iii) a presentation module for presenting the insight within the healthcare provider interface.

In some embodiments, the healthcare provider interface comprises a first plurality of portals. In some embodiments, at least one of the first plurality of portals comprises a patient context data grouping comprising the health data. In some embodiments, the health data is retrieved from an electronic medical record of the patient. In some embodiments, the patient context grouping comprises a second plurality of portals. In some embodiments, at least one of the second plurality of portals comprises an interactive timeline of a disease of the patient. In some embodiments, at least one of the second plurality of portals comprises interactive radiology imaging of the patient. In some embodiments, at least one of the second plurality of portals comprises a medical history of the patient and a current status of the patient. In some embodiments, at least one of the first plurality of portals comprises an outcomes navigator data grouping comprising the outcome data. In some embodiments, the outcomes navigator data grouping comprises a second plurality of portals. In some embodiments, at least one of the second plurality of portals comprises data relating to the similarly situated patient. In some embodiments, the data relating to at least one similarly situated patient comprises a treatment regimen of the at least one similarly situated patient. In some embodiments, at least one of the second plurality of portals is configured to present published data relating to the patient. In some embodiments, the data insights engine comprises a publication module for selecting the published data that is most relevant to the patient and for presenting the published data within the healthcare provider interface. In some embodiments, at least one of the first plurality of portals comprises an outcomes data grouping that comprises a second plurality of portals. In some embodiments, at least one of the second plurality of portals comprises a comparison of a performance of the healthcare provider to a performance of other healthcare providers. In some embodiments, the patient interface comprises a plurality of portals. In some embodiments, at least one of the plurality of portals comprises a format for entering the patient input. In some embodiments, the data insights engine comprises a machine learning software module. In some embodiments, the similarly situated patient comprises a patient sharing one or more of the following with the patient: (1) age, (2) gender, (3) race, (4) exposure, (5) co-morbidity, (6) diagnosis, (7) prognosis, (8) tumor pathology, (9) serum markers, (10) radiology findings, (11) family history, (12) surgical history, (13) treatment plan, (14) treatment regimen, and (15) treatment goal.

Described herein is a platform configured to provide treatment to a patient comprising:
  (a) a healthcare provider application comprising a healthcare provider interface configured to present data that assists the healthcare provider in providing the treatment to the patient;
  (b) a patient application comprising a patient interface configured to receive patient input from the patient regarding the treatment;
  (c) a third party interface configured to receive outcome data relating to the outcome of the treatment; and
  (d) a data insights engine comprising a machine learning algorithm configured to generate the data that assists the healthcare provider in providing the treatment to the patient.

In some embodiments, the healthcare provider interface comprises a first plurality of portals. In some embodiments, at least one of the first plurality of portals comprises a patient context data grouping comprising health data of the patient. In some embodiments, the health data is retrieved from an electronic medical record of the patient. In some embodiments, the patient context data grouping comprises a second plurality of portals. In some embodiments, at least one of the second plurality of portals comprises an interactive timeline of a disease of the patient. In some embodiments, at least one of the second plurality of portals comprises interactive radiology imaging of the patient. In some embodiments, at least one of the second plurality of portals comprises a medical history of the patient and a current status of the patient. In some embodiments, at least one of the first plurality of portals comprises an outcomes navigator data grouping comprising the outcome data. In some embodiments, the outcomes navigator data grouping comprises a second plurality of portals. In some embodiments, at least one of the second plurality of portals is configured to present data relating to at least one similarly situated patient identified by the data insights engine. In some embodiments, the data relating to at least one similarly situated patient comprises a treatment regimen of the at least one similarly situated patient. In some embodiments, at least one of the second plurality of portals is configured to present published data relating to the patient. In some embodiments, the data insights engine generates the data that assists the healthcare provider in providing the treatment to the patient by analyzing the patient input. In some embodiments, at least one of the first plurality of portals comprises an outcomes data grouping that comprises a second plurality of portals. In some embodiments, at least one of the second plurality of portals comprises a comparison of a performance of the healthcare provider to a performance of other healthcare providers. In some embodiments, the patient interface comprises a plurality of portals. In some embodiments, at least one of the plurality of portals comprises a means for entering the patient input. In some embodiments, the similarly situated patient comprises a patient sharing one or more of the following with the patient: (1) age, (2) gender, (3) race, (4) exposure, (5) co-morbidity, (6) diagnosis, (7) prognosis, (8) tumor pathology, (9) serum markers, (10) radiology findings, (11) family history, (12) surgical history, (13) treatment plan, (14) treatment regimen, and (15) treatment goal. In some embodiments, the third party comprises a payer and wherein the third party interface comprises a performance of a payer network that is determined based on the outcome data.

Described herein is a computer implemented method for treating a patient comprising:
  (a) ingesting with a machine learning software module:
    (i) health data of the patient;
    (ii) outcome data comprising an outcome of a similarly situated patient; and
    (iii) a patient input regarding the treatment;
  (b) analyzing the health data, outcome, data, and patient input thereby generating an analysis result;
  (c) generating a treatment insight based on the analysis result; and
  (d) presenting the treatment insight within a healthcare provider application.

In some embodiments, the healthcare provider application comprises a healthcare provider interface comprising one or more portals. In some embodiments, the health data is retrieved from an electronic medical record of the patient. In some embodiments, the outcome data comprises an outcome of a treatment regimen. In some embodiments, the patient input regarding the treatment comprises a request to modify one or more of a treatment plan, treatment regimen, or treatment goal. In some embodiments, the similarly situated patient comprises a patient sharing one or more of the following with the patient: (1) age, (2) gender, (3) race, (4) exposure, (5) co-morbidity, (6) diagnosis, (7) prognosis, (8) tumor pathology, (9) serum markers, (10) radiology findings, (11) family history, (12) surgical history, (13) treatment plan, (14) treatment regimen, and (15) treatment goal.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
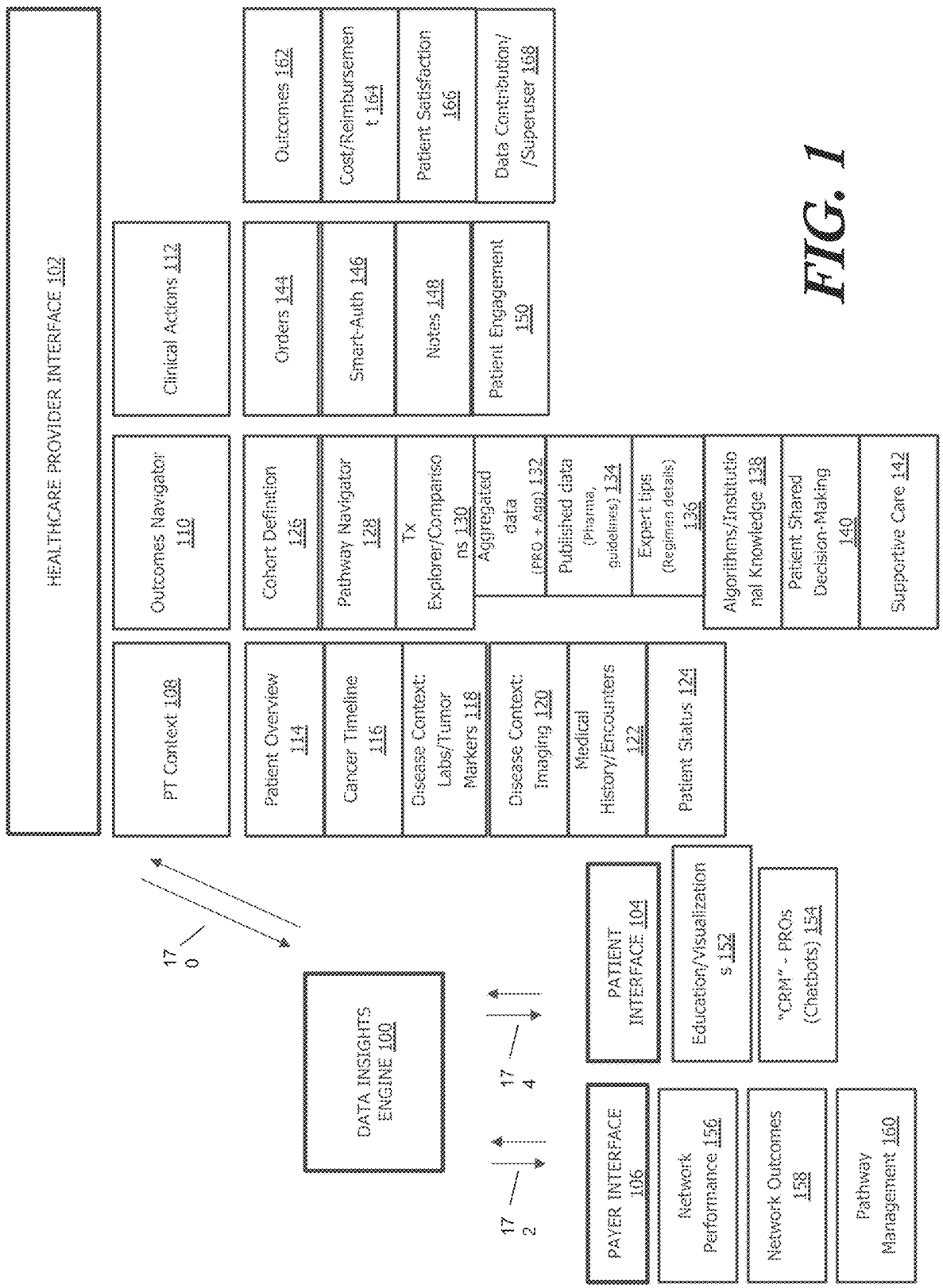
FIG. 1 shows a schematic representation of the architecture and organization of an exemplary embodiment of a platform as described herein.

Described herein are platforms and methods configured to provide treatment to a patient. While a platform as described here in embodiments is configured for treatment of oncology patients (i.e., patients with a cancer diagnosis), the embodiments of the platform described herein is useful in providing treatment to non-oncology patients as well.

While some exemplary embodiments described herein are described with reference to oncology patients, these exemplary embodiments are not meant to be limited to the treatment of oncology patients only.

Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise.

As used herein, a "treatment regimen" includes any medicament or medical procedure that could be used to treat a patient. Non-limiting examples of medicament types include chemotherapies, pain medications, anti-nausea medications, and antibiotics. Non-limiting examples of medical procedures include radiation therapy, surgery, physical therapy, and psychological therapy. A treatment regimen further includes within its scope any dosing of medicaments or scheduling of medical procedures to be provided to an individual. For example, a treatment regimen may include providing a chemotherapeutic agent twice a week to a patient at a certain dose per body weight of the patient. For example, a treatment regimen may include scheduling a surgery to excise a tumor followed by one month of once weekly chemotherapy. That is, a treatment regimen typically includes the details of the provision of a medicament and/or procedure in terms of, for example, quantities, frequency, order, and duration.

As used herein, a "treatment plan" includes a plan and organization of treatment with respect to a goal that is typically selected by both the healthcare provider and patient. For example, a treatment plan may be configured to provide the goal of curative treatment irrespective of side effects or treatment risks. Such a plan may be, for example, selected for younger patients with cancer types that are either curable or typically have longer periods of remission. For example, a treatment plan may be configured to provide the goal palliative care. Such a treatment plan may be, for example, selected for an older patient with a difficult to treat and/or incurable cancer type and may further take into account potential side effects and patient lifestyle preferences. That is, some patients may elect to forgo a more aggressive treatment plan in order to avoid resulting side effects that could limit their chosen life quality level.

As used herein a "patient" and an "individual" are often used interchangeably. Typically, these terms refer to a human or animal in need of treatment. Typically, the reason that the human or animal is need of treatment is to address a cancer.

As used herein a "portal" is a component of a software application configured to provide a user with a computer based format for interacting with data, wherein an interaction with data may comprise, for example, any interaction related to sight, touch, and/or sound. A portal, in some embodiments, comprises a graphic user interface. An example of a graphic user interface format for interacting with data comprises a webpage or webpage application that is, for example, html based. A portal, in some embodiments, includes a voice-recognition application for voice interaction by the user with the data associated with the portal. In some embodiments, a portal includes a software application for providing data audibly. In some of these embodiments, the portal is entirely configured for audible interaction with, for example, the data transmitted audibly to a user and a user interacting with the data through a voice recognition software application.

As used herein an "interface" is a component of a software application configured to provide a specific user with a customized computer based format for interacting with data, wherein an interaction with data may comprise, for example, any interaction related to sight, touch, and/or sound, and as used herein includes at least one portal. In addition to at least one portal, an interface, in some embodiments, includes additional customized portals as well as other content that is not provided via a portal. An interface, in some embodiments, comprises a graphic user interface. An example of a graphic user interface format for interacting with data comprises a webpage or webpage application that is, for example, html based. An interface, in some embodiments, includes a voice-recognition application for voice interaction by the user with the data associated with the portal. In some embodiments, an interface includes a software application for providing data audibly. In some of these embodiments, the portal is entirely configured for audible interaction with, for example, the data transmitted audibly to a user and a user interacting with the data through a voice recognition software application.

As used herein a "similarly situated patient" is a patient who shares some degree of commonality with another patient (such as, for example, a patient being treated by a healthcare provider who is using a platform as described herein). Non-limiting examples of features that a similarly situated patient may share with a patient being treated include (1) age, (2) gender, (3) race, (4) exposure, (5) co-morbidity, (6) diagnosis, (7) prognosis, (8) tumor pathology, (9) serum markers, (10) radiology findings, (11) family history, (12) surgical history, (13) treatment plan, (14) treatment regimen, and (15) treatment goal. It should be understood that with respect to some features, a similarly situated patient may not have the exact identical feature as another patient but may instead be similar to that feature. For example, within the scope of a similarly situated patient determined to be similarly situated based on age is, for example, a similarly situated patient who is 2 years younger than a patient being treated.

Need for an Oncology Patient Specific Platform

Described herein is a platform configured to improve the existing way in which healthcare is provided to patients. While the platforms described herein are configured to improve the existing way in which healthcare is provided to all patients, there is a particular need for such a platform with respect to oncology patients.

Namely, the existing manner in which healthcare is provided to oncology patients is among other things:
(1) overly complex in terms of decision making,
(2) does not assist healthcare providers in decision making or treatment provision,
(3) is not sufficiently data-driven,
(4) does not sufficiently solicit or take into account patient feedback, and
(5) does not effectively provide useful data to healthcare payers and pharmaceutical developers.

Existing Treatment Decision-Making is Overly Complex

Currently, the existing treatment decision-making pathway for healthcare professions is overly complex. That is, the process of choosing the proper (1) treatment regimen (which includes, for example, any medicament or medical procedure that could be used to treat a patient as well as dosing of medicaments or scheduling of medical procedures to be provided to an individual) and (2) treatment plan (which includes, for example, a plan and organization of treatment with respect to a goal that is typically selected by both the healthcare provider and patient) for a patient is extremely complex, and as a result healthcare providers are struggling to provide proper care to their patients.

The complexity around selecting one or more of a treatment regimen and treatment plan in today's existing healthcare paradigm is at least in part due to the (1) relatively large amount of information that a healthcare provider must process in order to reach the optimal decision and (2) the unique nature of every cancer and every patient.

With respect to selecting treatment regiments, in the field of oncology in particular, there are a large amount of new therapeutics and modalities being developed and made publicly available on a regular basis. New drugs are constantly being developed and studied and old drugs are being deemed less efficacious. Surgery in some cases is recommended and in other cases, new studies may reveal that non-surgical treatment is superior or that surgery with adjuvant therapy is best. And, sometimes study findings seem to contradict one another. That is all to say, that with respect to selecting an optimal treatment regimen for a patient, healthcare providers must themselves keep up with constantly newly developed treatment modalities being released and then sort through a barrage of constantly newly generated study data in order to determine which modality serves his or her patients best. In the field of oncology in particular, this is an extremely difficult task. Add to that, the fact that it is generally believed that "no two cancers are alike" in the sense that, for example, even the same cancer type may have very differently behaving subtypes and each patient may behave differently with the same cancer due to, for example, their age or genetic makeup. Additionally, there is constantly changing data with respect to dosing and the provision of adjuvant therapy along with surgery. Not uncommonly, there is no single regimen that suits all patients, but rather it is often the case that each patient needs an individualized treatment regimen. For example, some patients due to suffering strongly from side effects do not tolerate a recommended treatment modality and will need to have a custom treatment regimen developed.

With respect to selecting treatment plans, there is often imperfect data available as to how to customize a particular treatment to achieve a specific healthcare provider and/or patient goal. Sometimes, there is imperfect communication between the healthcare provider and the patient as to what the treatment goal is.

The platform described herein, in contrast, is configured to at least address the above issues in order to simplify and optimize the existing overly complex treatment decision-making process for healthcare providers treating their patients. As will be described, the instant platform is configured, in some embodiments, to at least (1) help healthcare providers navigate the overwhelming amount of data available to them with respect to healthcare related decisions and (2) address the unique nature of each cancer and each patient.

Existing Treatment Software Applications do not Provide Sufficient Assistance to Healthcare Providers in Terms of Decision Making Existing treatment software applications do not provide sufficient assistance to healthcare providers in terms of decision making. As described herein, an "existing treatment software application" includes any computer based application, software, platform, and/or system configured to provide a user interface for healthcare providers that is configured to assist the healthcare providers in terms of patient decision making. That is, existing treatment software applications do not (1) aggregate data and/or (2) digest and present data in a manner that is useful to healthcare providers.

For example, existing treatment software applications do not have the ability to aggregate large amounts of data, where data includes patient data from Electronic Medical Records (EMR) as well as data generated by clinical studies. The typical existing treatment software application platform is either lacking in patient EMR data or lacking in clinically derived data or both. As such, healthcare providers often must find data that they need to assist with their decision making on their own, and at least in the case of patient EMR data, are often limited in terms of what they can access.

For example, even when existing treatment software applications have access to certain types of data, they are typically unable to process the data and present it in a manner that actually assists healthcare providers in terms of decision making. That is, often the data aggregated by the existing treatment software applications is presented in a form that doesn't assist the healthcare provider in terms of his or her decision making because, for example, the existing treatment software applications do not make clear how the presented data relates to a particular individual being treated by the healthcare provider.

The platform described herein, in contrast, is configured, in some embodiments, to aggregate large amounts of data and, in some embodiments, to analyze aggregated data using advanced analytics and machine learning in order to provide healthcare providers with information that will directly assist the healthcare provider in terms of decision making.

Existing Healthcare Decision Making is not Sufficiently Data Driven

Existing decision making processes are not sufficiently data driven. That is, oncologists typically do not frequently consider data when making treatment decisions. In part, this is due to the issues already described in terms of the complexity of the current paradigm as well as healthcare providers not having access to data because of an absence of data and inadequate data presentation. Additionally, some of the lack of application of data in decision making also arises from healthcare providers not trusting data or believing that data should not necessarily be consulted when making healthcare related decisions.

In some embodiments, the instant platform creates an interface for healthcare providers that integrates data (and in particular aggregated and analyzed data) into the interface in a manner that healthcare providers trust and are willing to incorporate into their decision making. In some embodiments, a platform as described herein provides a healthcare provider with patient information relating to similarly situated patients to the patient the healthcare provider is treating. In these embodiments, the platform provides specific outcome data for the therapy pathway selected for the similarly situated patient.

Existing Treatment does not Sufficiently Consider Patient Feedback in Decision Making Existing healthcare provided decision making does not sufficiently consider patient feedback. For example, with oncology patients in particular, treatment may take place over a relatively long period of time, as opposed to a discrete treatment, and patient needs may change. Often it is the case that the treating healthcare provider initiates a treatment regimen for the patient and does not waiver from the treatment regimen, while the patient may in fact have a need for the healthcare provider to do so. For example, a patient may not have realized the severity of the side effects associated with a particular treatment regimen and desires that it be modified. For example, the patient may have an event during their treatment regimen that they wish to attend and that would require them to pause their regimen. Another example of when a patient's input may not be sufficiently considered is with respect to the initial choice of the treatment regimen wherein a patient may wish to achieve a certain goal with the treatment and the healthcare provider fails to match the treatment regimen for the patient with the goal that the patient wishes to achieve.

The instant platform, in contrast, in some embodiments, provides a patient interface in the form of, for example, a portal in which the patient is asked to provide feedback that is used by the platform to guide the healthcare provider. In this manner, the platform, in these embodiments, is integrating patient input into how the platform interacts with the healthcare provider in order to incorporate patient feedback and needs into the healthcare decision making process.

Existing Treatment does not Effectively Provide Useful Data to Healthcare Payers and Pharmaceutical Developers There is a need for improved communication of information from the clinics to third parties such as payers and pharmaceutical and medical device developers. Often times, third parties must wait to obtain data from studies, which creates a lag time between the outcomes to patients and the arrival of the data to the third party.

In contrast, the instant platform, in some embodiments, includes third parties within the platform so that they are able to access data directly as well as input data of their own into the platform.

Platform Overview

In general, a platform as described herein is configured to assist a healthcare provider in providing treatment to a patient. More specifically, a platform is configured to assist a healthcare provider in selecting a treatment for a patient. In some embodiments, a platform is also configured to assist a healthcare provider in executing a selected treatment for a patient. In some embodiments, a platform is further configured to assist a healthcare provider in diagnosing a patient.

In general, a platform as described herein comprises a computer implemented or software based system that comprises one or more user applications. For example, in some embodiments, a user application comprises a healthcare provider application which is configured to be used by a healthcare provider.

A platform, in some embodiments, includes a patient application.

In some embodiments, a platform includes a third party application, where a third party is a party involved in providing healthcare to patients. Non-limiting examples of third parties that may have a third party application integrated with embodiments of the platforms described herein include healthcare payers, pharmaceutical developers, medical device developers, research institutions, and hospitals.

In general, a platform as described herein comprises a processing component configured to ingest data, process data, and output an insight regarding said data or an insight related to a patient.

A processing component, in some embodiments, comprises software having one or more modules configured to carry out one or more of the tasks of (1) ingesting data, (2) processing data, and (3) outputting an insight regarding said data, an insight related to a patient, or an insight relating to both. In some embodiments, software suitable for use with a platform as described herein comprises a machine learning algorithm.

Data Ingestion

In some embodiments, a platform comprises a data ingestion module configured to ingest data into the platform's processing component. In some embodiments, a platform's processing component comprises a data insights engine and an ingestion module is a component of a data insights engine.

In some embodiments, data is manually provided by an individual to the data ingestion module which is configured to receive said manually inputted data. For example, in some embodiments, a user such as a healthcare provider, patient, or third party provides data to the ingestion module by entering data into an application or portal via typing on a keyboard, keypad, and/or touch screen.

For example, in some embodiments, a user such as a healthcare provider, patient, or third party provides data to the ingestion module by transmitting the data via email, text, and/or by voice (i.e., by speaking).

In some embodiments, a data ingestion module is configured to either retrieve or receive data from one or more data sources, wherein retrieving data comprises a data extraction process and receiving data comprises receiving transmitted data from an electronic source of data.

For example, some embodiments of the platforms described herein are configured to retrieve or receive data from many different data sources such as wearable devices, EMR providers, and DNA providers. In some embodiments, the platform is configured to ingest data from a plurality of wearable devices and applications, and many health providers that are hosted on EMR vendors, non-limiting examples of which include Epic, Cerner, AllScripts, AthenaHealth, and VA (HealtheVet), as well as the raw genome-wide genotyping data provided by direct-to-consumer DNA labs including, by way of examples, 23andMe, Ancestry.com, MyHeritage, and FamilyTreeDNA. In some embodiments, coding system data such as, for example, ICD-9/10 data is extracted by the ingestion module.

In some embodiments, data that is ingested by the platform is sorted based on, for example, data type. In some embodiments, the data insights engine determines how to sort the data based on various factors such as, for example, the healthcare provider and/or the patient of the healthcare provider.

In some embodiments, data that is ingested by the platform is cleaned. In these embodiments, data is cleaned in the sense that corrupt data is either corrected or deleted. Examples of corrupt data include, for example, incorrectly entered or misfiled data. For example, corrupt data to be cleaned includes typographical errors and inaccurate data.

Figure 10:
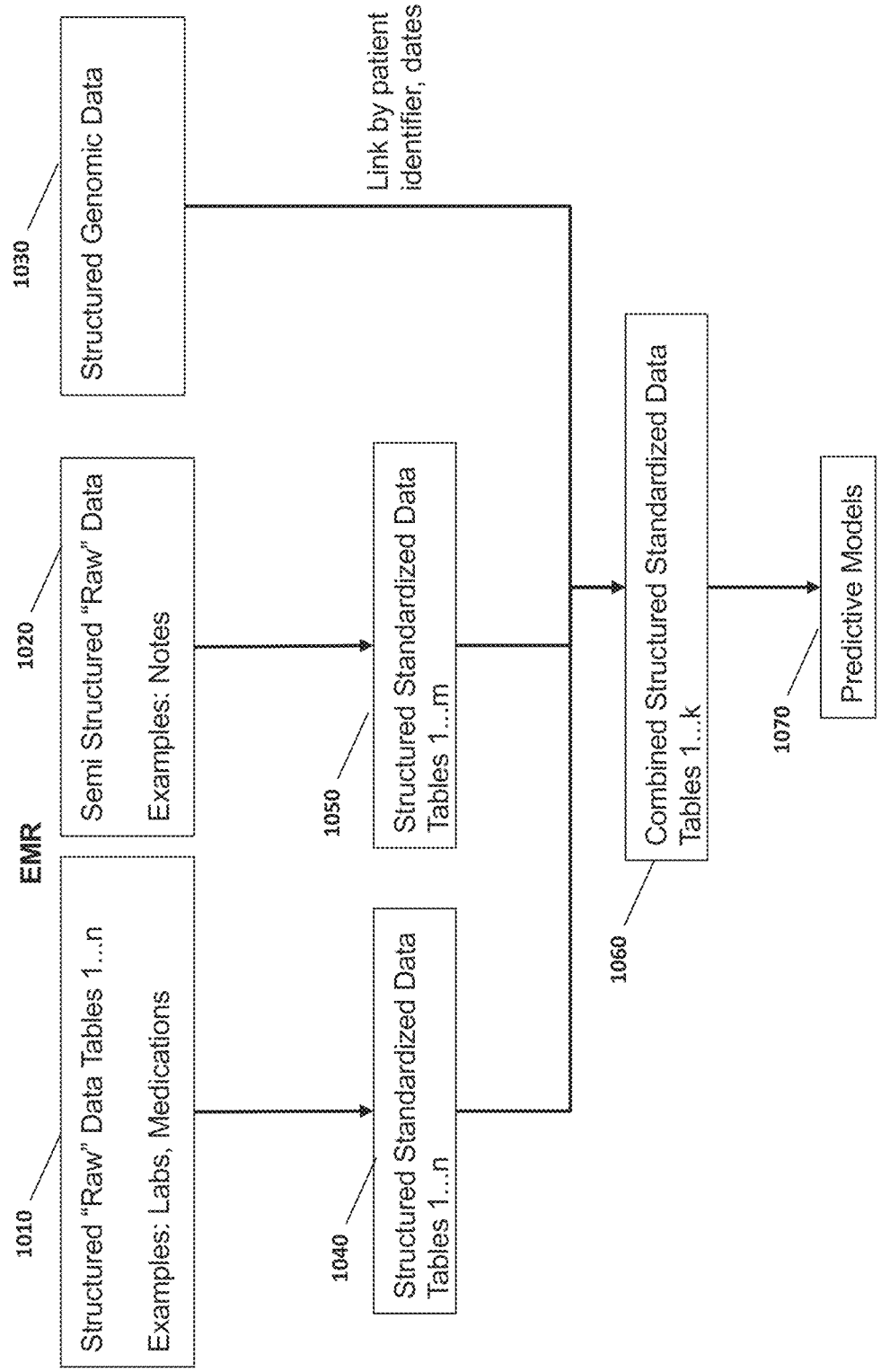
FIG. 10 shows an example of a data extraction process that incorporates natural language processing to standardize data inputs for data processing and analysis using predictive models.

In some embodiments, data is extracted from one or more data sources. An example of a data extraction process is illustrated in FIG. 10. The data source(s) include structured raw data 1010, semi-structured raw data 1020, structured genomic or genetic data 1030, or any combination thereof. Examples of structured raw data include laboratory tests/results and medications or prescriptions, which can include information such as lab names, medication names, and other associated information. Semi-structured raw data can include less structured information such as doctor's notes from a patient consultation or treatment checkup. Structured genomic data can include results of targeted biomarker testing or large-scale tests such as whole genome sequencing. For example, the organized results of a mutation panel of the top 100 cancer genes is an example of structured genome data (e.g., a table listing the genes with corresponding mutation status).

In some embodiments, data is extracted from one or more data sources using natural language processing (NLP). One NLP approach is rule-based NLP which applies various automated rules to standardize and/or format the sourced data into a common standard that is compatible with downstream data processing and/or analysis. For example, the structured laboratory results may be evaluated to identify keywords associated with each standardized lab name or medication name. The rules can also apply unit conversion logic or check for internal consistency, for example, cross-reference the data to determine if a medical checkup or treatment administration date is consistent across parts of the same medical record or different medical records. A detected inconsistency may be resolved using one or more rules or alternatively flagged for manual resolution. These rules may be curated by a user based on the particular domain to which the data belongs (e.g., lab test or prescription). In some cases, the application of automated rules to the data enables detection of inconsistent values that are flagged. For example, in one scenario, a treatment table shows medication X given on date A for Cycle 2 and date B for Cycle 3, but date B is before date A. In this case, the flagged error may be auto-corrected by referencing the Visit table and determining when visits were scheduled for the cycles of treatment. Accordingly, the information extracted from the structured raw data 1010 and/or semi-structured data 1020 can be converted into structured standardized data 1040, 1050.

Another NLP approach utilizes supervised machine learning to annotate one or more portions of the raw text with gold standard labels. For example, a name in the raw data may correspond to a standardized name. A training data set including labeled text is used to train a NLP ML model. As an example, NLP models can be used to extract adverse events, treatment response, and other relevant medical information from an electronic medical record (EMR) into one or more controlled or standardized vocabularies (e.g., MedDRA, RECIST). Internal consistency checks can also be performed as described herein. Accordingly, the information extracted from the structured raw data 1010 and/or semi-structured data 1020 can be converted into structured standardized data 1040, 1050.

Another NLP approach does not use gold standard labeling, but instead combines the previous two NLP approaches by generating rules based on the raw data, and then using the rules to train a model to apply to the raw data during the standardization/formatting process. Instead of training the NLP model on human annotated gold standard labels, the NLP model is trained based on agreement between the rules. An advantage of this approach is it enables models to be constructed without requiring a manual annotation process which can be time-consuming. This approach is applicable to the conversion of structured raw data 1010 and/or semi-structured data 1020 into structured standardized data 1040, 1050. Any combination of the NLP approaches disclosed herein can be used to standardize the input data received from various data sources. Various tools can be used to implement the NLP approaches described herein, including open source NLP packages such as, for example, Snorkel. As an example, clinical data expertise is used to create a large number of rules based on the observed data structure. An advantage of this approach is that the accuracy of the individual rules does not need to be high. The rules are then used to score records by applying each rule to each record, creating a matrix of rule outputs. The model is then trained iteratively via an algorithm that upweights rules that agree in their output for a plurality of records, and downweights rules that tend to disagree with other rules. The output of the model is a weighted set of rules where essentially each rule contributes a weighted vote on the best data standard for a record. Together, the weighted combination of rules form a data standardizing function that has been learned from multiple eligible component parts. Accordingly, the NLP model can be configured to effectively standardize and/or process input data even though the individual rules used to score records lack a high accuracy.

Data Processing

In some embodiments, a processing component of a platform comprises a data insights engine. A data insights engine is generally an algorithm (or software module) that analyzes ingested data and provides an insight related to the ingested data or a patient being treated based on the analysis.

In some embodiments, a data insights engine comprises artificial intelligence software or a machine learning algorithm (or software module).

In some embodiments, the data insights engine comprises one or more machine learning algorithms or models configured to predict individual outcome. Outcomes can include patient survival (e.g., 5-year survival), progression (e.g., degree of cancer progression), adverse event (e.g., neutropenia), or other relevant outcome metrics. The outcome can relate to a cancer such as, for example, colorectal cancer, breast cancer, lung cancer, prostate cancer, hepatocellular cancer, gastric cancer, pancreatic cancer, cervical cancer, ovarian cancer, liver cancer, bladder cancer, urinary tract cancer, thyroid cancer, renal cancer, carcinoma, melanoma, or brain cancer. The outcome may be related to one or more therapeutic treatments. The treatment can include one or more of chemotherapy, hormone therapy, targeted therapy, radiation therapy, stem cell transplant, surgery, or immunotherapy.

In some embodiments, the adverse event comprises hospitalization caused by one or more side effects of a particular treatment or therapy. In some embodiments, the adverse event comprises discontinuation of the therapy caused by one or more side effects. In further embodiments, the one or more side effects are selected from the group consisting of: neutropenia, leucopenia, thrombocytopenia, fatigue, pain, mucositis, skin rash, nausea, vomiting, constipation, diarrhea, cognitive dysfunction, nerve damage, appetite loss, organ damage, and any combination thereof. In some cases, the adverse event comprises a serious adverse event such as death, a life-threatening side effect, hospitalization, disability, or permanent impairment or damage.

Figure 11:
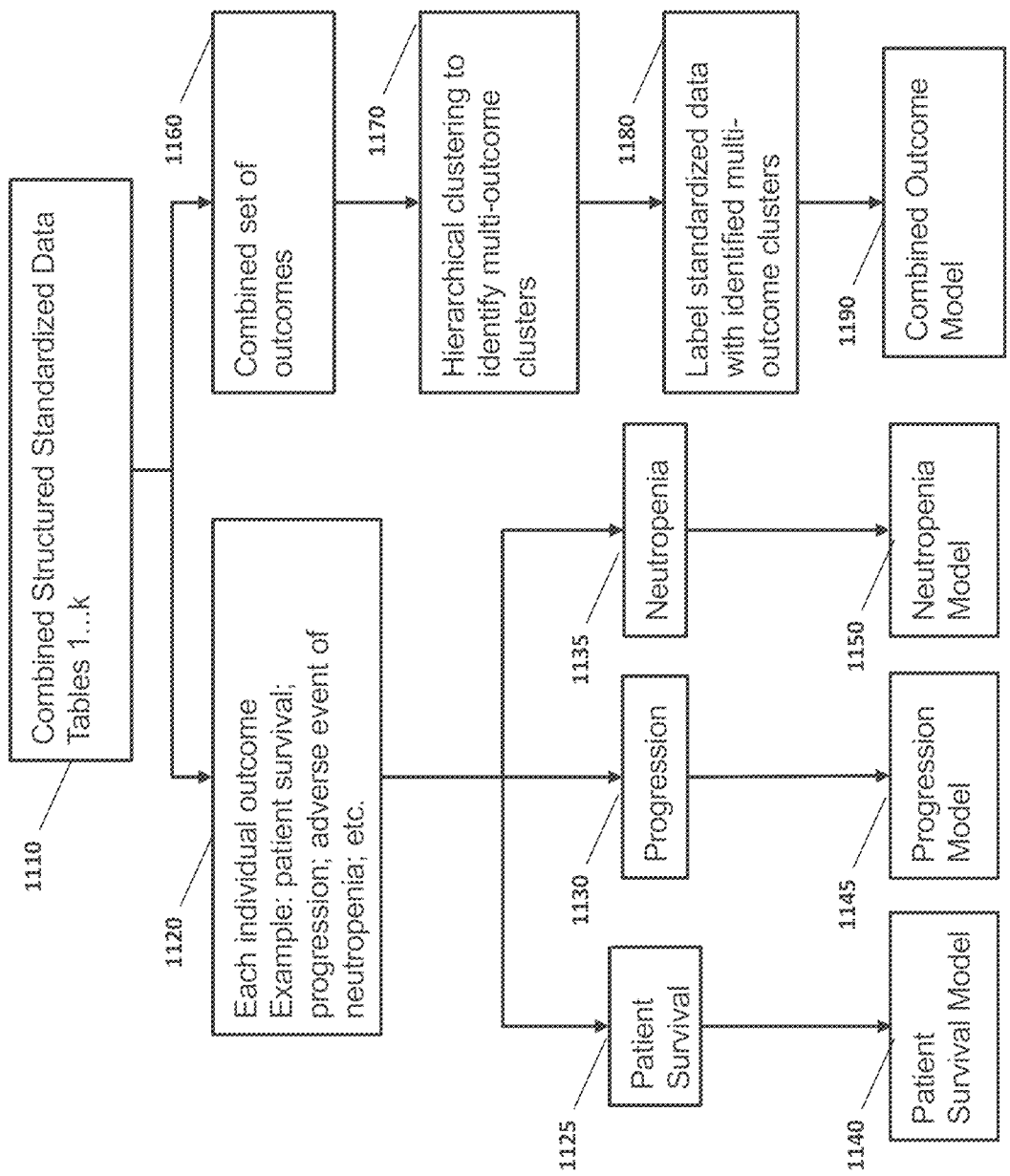
FIG. 11 shows an analytical framework using machine learning model(s) to process and analyze standardized data inputs in order to generate predictions.

The one or more machine learning algorithms or models configured to predict individual outcomes can be implemented using a variety of model types. Model types suitable for this analysis include random forest, gradient boosted trees, penalized linear regression, penalized logistic regression, cox regression, and recurrent neural network. A machine learning model can be trained using a training data set comprising patient information labeled with outcomes. The trained model can then generate one or more predictions for the individual outcome(s). Each outcome may be ranked according to predictive confidence or accuracy. The data insights engine can identify the highest ranked outcome. In some cases, the engine outputs an insight comprising the highest ranked outcome. Non-limiting examples of this process are illustrated in FIG. 11. The combined structured and standardized data 1110 is used to model each individual outcome 1120, for example, patient survival 1125, progression 1130, and/or neutropenia 1135. The corresponding trained patient survival model 1140, progression model 1145, and neutropenia model 1150 are thus configured to predict individual outcomes.

In some embodiments, the data insights engine comprises one or more machine learning algorithms or models configured to generate outcome predictions based on combined sets of outcomes. This approach utilizes a unique two-step process in which patient cohorts are first clustered based on multiple outcomes, and then a model is trained to predict the multi-outcome clusters.

The multi-outcome predictive process can use hierarchical clustering to identify patient cohorts that share common outcomes. The combined structured and standardized data 1110 is labeled according to the various possible outcomes and/or outcome categories 1160. Hierarchical clustering as described herein is applied to the data set to identify multi-outcome clusters representing various patient cohorts 1170. Next, the standardized data is labeled with the multi-outcome clusters identified in the previous step 1180. Finally, a combined outcome model 1190 is trained using the standardized data labeled with the multi-outcome clusters. As a non-limiting example, one possible cluster is patients who experience early severe adverse events but recover and then go on to have a good efficacy outcome. These clusters are empirically determined based on the clustering algorithm and are not predefined. Thus, the clustering is objectively determined based on empirical evidence and less subject to human bias. Oftentimes, each cancer/treatment is found to have between 4-10 such patient cohorts. A training data set is then labeled according to the multi-outcome clusters identified in the first step. This cluster-labeled training data set is then used to train a machine learning model during a second step. This trained machine learning model is thus configured to predict the cluster to which a new patient belongs. Various models are suitable for cluster prediction such as, for example, random forest, gradient boosted trees, and penalized multinomial regression.

In some embodiments, the hierarchical clustering incorporates weights based on user input (e.g., patient and/or healthcare provider input). In individual patient can provide input such as preference for certain outcomes over others that is taken into account by the clustering/modeling process. For example, in the case of a patient who has a strong preference for certain outcome(s), a relatively strong weight (e.g., higher weight than other outcomes) can be assigned for the preferred outcome and a relatively low weight for nonpreferred outcome(s) (e.g., lower weight than the preferred outcome(s)). The weight is incorporated into the clustering to define cohorts. Since hierarchical clustering is based on distance metric between outcomes, the implementation of weighting within hierarchical clustering framework is accomplished through the use of a weighted distance metric where certain outcomes were more influential in the distance, thus making them more influential in the clustering calculations. Accordingly, the hierarchical clustering may be weighted to account for individual preferences.

In some embodiments, a machine learning algorithm (or software module) of a platform as described herein utilizes one or more neural networks. A neural network is a type of computational system that can learn the relationships between an input data set and a target data set. A neural network is a software representation of a human neural system (e.g., cognitive system), intended to capture "learning" and "generalization" abilities as used by a human. In some embodiments machine learning algorithm (or software module), the machine learning algorithm (or software module) comprises a neural network comprising a convolutional neural network. Non limiting examples of structural components of embodiments of the machine learning software described herein include: convolutional neural networks, recurrent neural networks, dilated convolutional neural networks, fully connected neural networks, deep generative models, and Boltzmann machines.

In some embodiments, a machine learning software module comprises a recurrent neural network software module. A recurrent neural network software module is configured to receive sequential data as an input, such as consecutive data inputs, and the recurrent neural network software module updates an internal state at every time step.

In some embodiments, a machine learning software module comprises a supervised or unsupervised learning method such as, for example, SVM, random forests, clustering algorithm(s) (or software module(s)), gradient boosting, logistic regression, and/or decision trees.

In some embodiments, a machine learning software module comprises a neural network comprising a CNN, RNN, dilated CNN, fully connected neural networks, deep generative models and deep restricted Boltzmann machines.

In some embodiments, a neural network is comprised of a series of layers termed "neurons." In some embodiments, a neural networks comprises an input layer, to which data is presented; one or more internal, and/or "hidden," layers; and an output layer. A neuron may be connected to neurons in other layers via connections that have weights, which are parameters that control the strength of the connection. The number of neurons in each layer may be related to the complexity of the problem to be solved. The minimum number of neurons required in a layer may be determined by the problem complexity, and the maximum number may be limited by the ability of the neural network to generalize. The input neurons may receive data from data being presented and then transmit that data to the first hidden layer through connections' weights, which are modified during training. The first hidden layer may process the data and transmit its result to the next layer through a second set of weighted connections. Each subsequent layer may "pool" the results from the previous layers into more complex relationships. In addition, whereas conventional software programs require writing specific instructions to perform a function, neural networks are programmed by training them with a known sample set and allowing them to modify themselves during (and after) training so as to provide a desired output such as an output value. After training, when a neural network is presented with new input data, it is configured to generalize what was "learned" during training and apply what was learned from training to the new previously unseen input data in order to generate an output associated with that input.

In some embodiments of a machine learning software module as described herein, a machine learning software module comprises a neural network such as a deep convolutional neural network. In some embodiments in which a convolutional neural network is used, the network is constructed with any number of convolutional layers, dilated layers or fully connected layers. In some embodiments, the number of convolutional layers is between 1-10 and the dilated layers between 0-10. In some embodiments, the number of convolutional layers is between 1-10 and the fully connected layers between 0-10.

Data Output

In general, a data insights engine of a platform as described herein outputs an insight based on data analyzed using artificial intelligence software or a machine learning algorithm (or software module) as described herein. An insight outputted by the data insights engine generally relates to inputted data, one or more patients, or both.

An output of a data insights engine, in some embodiments, is presented to a healthcare provider via a healthcare provider application which may further comprise a healthcare provider interface.

An output of a data insights engine, in some embodiments, is presented to a patient via a patient application which may further comprise a patient interface.

An output of a data insights engine, in some embodiments, is presented to a third party via a third party application which may further comprise a third party interface.

For example, in some embodiments an insight generated by a data insights engine of a platform as described herein comprises an identification of a patient who is similarly situated to the patient of a healthcare provider who is using the platform. A patient who is similarly situated may be, for example, a patient with the same cancer diagnosis as the patient. A patient who is similarly situated may be, for example, a patient with the same demographic information as the patient. A patient who is similarly situated may be, for example, a patient who either completed or is undergoing the same treatment regimen as planned for the patient. It should be understood that a first patient may be deemed similarly situated to another patient such as a patient of the healthcare provider using the platform for numerous reasons and based on one or more factors and the examples presented here are not intended to be limiting. It should further be understood that a plurality of similarly situated patients may be identified in the same manner as identifying a single similarly situated patient and reference to a single similarly situated patient should not be understood to be limited to one single patient only but in some embodiments includes a plurality of similarly situated patients. Lastly, it should be understood that, in some embodiments, a similarly situated patient comprises a composite of a plurality of patients. In these embodiments, once identified, a similarly situated patient along with their health data are presented to a healthcare provider treating the patient.

Health data of a similarly situated patient presented to a healthcare provider by a data insights engine as described herein may, for example, include the diagnoses, treatment regimen, and outcome of the similarly situated patient. Non-limiting examples of health data presented to a healthcare provider by a data insights engine as described herein may, for example, include pathology reports, medicament dosing, types of diagnostic and therapeutic procedures performed, and the outcomes of said diagnostic and therapeutic procedures. For example, a diagnostic procedure may comprise a radiographic study of the similarly situated patient such as a CT scan, which may be presented to the healthcare provider by the data insights engine. For example, diagnostic procedures may comprise a laboratory study of the similarly situated patient such as blood work, the results of which may be presented to the healthcare provider. In this way, a healthcare provider is provided with examples of patients and their accompanying health data that the healthcare provider can use to assist him or her in determining or adjusting a treatment regimen for the patient. For example, a healthcare provider may select a treatment regimen for the patient based on a treatment regimen provided to a similarly situated patient that the healthcare provider deems to be most similar to the patient. In some of these embodiments, a data insights engine is configured to determine how relevant the health data of a similarly situated patient may be to said healthcare provider based on information relating to the healthcare provider's practice and/or relating to the patient. For example, in some embodiments, if a data insights engine determines that a healthcare provider is mostly treating a certain type of patient and has less experience treating a patient having the attributes of the patient, the data insights engine will determine that said health data of a similarly situated patient is relevant to the healthcare provider and provide said information to him or her. In some embodiments, said data insights engine will further determine a degree of relevance to the healthcare provider expressed as a percentage and present the percentage to the healthcare provider as well. It should be noted that in this and other embodiments, a data insights engine presents outputs that assist a healthcare provider in making a treatment decision without suggesting a specific decision for the healthcare provider to make. That is, in these embodiments, the data insights engine provides an output that provides assistance to the healthcare provider without necessarily making a specific suggestion. In this way, the healthcare provider's decision making process is enhanced through the advanced analytics of the data insights engine without having the data insights engine effectively replace the decision making process by outputting to the healthcare provider what he or she should do. Assisting the healthcare provider in the decision making process rather than pointing to a decision to be made will promote broad acceptance from healthcare providers who typically desire to maintain independence and autonomy in their healthcare related decision making processes.

In some embodiments, an insight generated by a data insights engine of a platform as described herein comprises one or more treatment regimens. For example, a data insights engine may present a treatment regimen to a healthcare provider that was deemed successful for a similarly situated patient. A treatment regimen may be deemed successful, in some embodiments, when a goal of the patient is achieved through the application of the treatment regimen. In some embodiments, a treatment regimen is presented to a healthcare provider based on data received by the data insights engine from a study. For example, a data insights engine, in some embodiments, ingests and analyzes study data from, for example, a study of the effect of a pharmaceutical provided to human patients and provides information regarding said pharmaceutical to a healthcare provider based on said analysis in order to assist said healthcare provider in treating a patient. For example, a data insights engine, in some embodiments, ingests and analyzes study data from, for example, a study of the effect of a surgical procedure provided to human patients and provides information regarding said surgical procedure to a healthcare provider based on said analysis in order to assist said healthcare provider in treating a patient. For example, a data insights engine, in some embodiments, ingests and analyzes study data from, for example, a study of outcome data of patients having, for example, a certain type of cancer or a cancer in a certain stage and provides information regarding said study to a healthcare provider based on said analysis in order to assist said healthcare provider in treating a patient. In some of these embodiments, a data insights engine is configured to determine how relevant said information may be to said healthcare provider based on information relating to the healthcare provider's practice and/or relating to the patient. For example, in some embodiments, if a data insights engine determines that a healthcare provider is providing a treatment regimen to a patient that is deemed less effective than a treatment regimen based on study data, in some embodiments, the data insights engine will determine that said information is relevant to the healthcare provider and provide said information to him or her. In some embodiments, said data insights engine will further determine a degree of relevance to the healthcare provider expressed as a percentage and present the percentage to the healthcare provider as well. The degree of relevance would be based on two factors: a) the data insights confidence in the result determined via cross validation, and b) the degree to which the patient is similar to the patients where the insight is drawn from (based on hierarchical clustering or other distance based method). Again, it should be noted that in this and other embodiments, a data insights engine presents outputs that assist a healthcare provider in making a treatment decision without suggesting a specific decision for the healthcare provider to make. In this way, the healthcare provider's decision making process is enhanced through the advanced analytics of the data insights engine without having the data insights engine effectively replace the decision making process by outputting to the healthcare provider what he or she should do. Assisting the healthcare provider in the decision making process rather than pointing to a decision to be made will promote broad acceptance from healthcare providers who typically desire to maintain independence and autonomy in their healthcare related decision making processes.

In some embodiments, an output of a data insights engine comprises a prediction of an outcome for an individual or a group of individuals. An outcome that is predicted may be, for example, a result of a treatment, a result of a disease, or associated with a treating physician or healthcare facility. Outcomes may, in some embodiments, be classified in terms of, for example, safety outcome or efficacy outcome. For example, a safety outcome may be assessed in terms of whether a treatment harmed an individual receiving it through, for example, a side effect. For, example, an efficacy outcome may be determined if, for example, a treatment prolongs a life of an individual receiving being treated beyond an expected life expectancy. In some embodiments, an outcome is predicted by determining a similarity between an individual (or group of individuals) whose outcome is to be predicted and an individual (or group of individuals) having a known outcome. In these embodiments, when an individual (or group of individuals) share certain key predictive characteristics with an individual (or group of individuals) with known outcomes, it is predicted that the individual (or group of individuals) will share the same outcome as the individual (or group of individuals) whose outcome is known. For example, a first patient having certain tumor marker is compared, in some embodiments, to a second patient having the same tumor marker and a known outcome and it is predicted that the first patient will have the same outcome as the second patient based on sharing the characteristic of having the same tumor marker.

In some embodiments, one or more machine learning software modules are used to analyze patient characteristics and identify which one or more characteristics are most impactful with respect to a prediction. That is, in some embodiments, one or more machine learning software modules determine factors including patient related characteristics that are associated with or likely result in a particular outcome. In these embodiments, identification of these factors or characteristics is used to make predictions with respect to outcomes in other similarly situated patients based presence, absence, and/or degree of presence or absence of a particular factor or characteristic.

In some embodiments, the identification of factors and or characteristics is performed by one or more software modules which, in some embodiments, comprise one or more machine learning modules. Such software modules are configured to cluster (or group) individuals (or groups of individuals) in order to identify factors (e.g., environmental or personal) and/or characteristics (e.g., personal) that are associated with or cause a particular result or outcome. In some embodiments, a data insights engine comprises (or is operatively linked to) one or more software modules (which in some embodiments comprises one or more machine learning software modules) that are configured to cluster (or group) a plurality of individuals based on outcomes (e.g., treatment outcomes and/or disease outcomes). Once clustered by outcomes, the individuals or populations within each cluster of outcomes are analyzed by the one or more software modules with respect to common factors and/or characteristics to determine which characteristics within the group of individuals clustered by common outcome is a characteristic that is associated with or determinative of the outcome shared by the individuals in the group/cluster. In general, in these embodiments, the approach to determining factors and characteristics useful in making predictions is achieved by first achieving the grouping of outcomes as described herein. It should be understood that there are numerous methods suitable for achieving grouping or clustering of outcomes in order to identify factors and/or characteristics associated with or that result in an outcome.

An exemplary approach to the clustering (or grouping) of individuals with similar outcomes is an insights engine that comprises or is operatively coupled with a software module that applies a hierarchical clustering technique to a data set. Hierarchical clustering in general is a process wherein distances between data points to be clustered (e.g., outcomes) are determined and wherein data points that are determined to be closest to each other are clustered.

A hierarchical clustering technique, in some embodiments, first identifies at least two data points (e.g., outcomes) that are closest to one another and clusters them together. In a next step, it determines a distance from a third data point to the clustered original two data points. If that third data point is closest to the clustered original two data points, it will cluster that third data point with the first two. If on the other hand, that third data point is closer to a fourth data point than it is to the cluster of the first two data points, the third and fourth data points are clustered and a distance is determined between the first cluster (the first two data points) and the second cluster (the third and fourth data points). Ultimately, a hierarchical clustering technique determines distances between all the data points being analyzed and establishes a hierarchical relationship among all of the data points based on distances that are respectively apart from one another. A dendrogram (or cluster tree) is one type of visual representation of hierarchical relationships between data points in a hierarchical clustering algorithm.

In hierarchical clustering, a distance metric determines the clusters. In some embodiments, a distance metric is set by a user. In some embodiments, a distance metric is set by the algorithm itself. When the algorithm itself sets the distance metric for the data points, in some embodiments, the algorithm is a learning algorithm that determines the distance metric for particular data based on previous learning/training.

In some embodiments, a software module as described herein utilizes a hierarchical technique that groups individuals (or populations of individuals) based on an outcome for the individual (or population of individuals) and the outcome comprises an efficacy of a treatment. For example, in some embodiments, an outcome comprises a survival time following the initiation of a treatment. In this manner, an outcome represents an efficacy of a treatment with respect to the treatment's effect on survival time. An outcome, in some embodiments, comprises a safety metric associated with a treatment. For example, an outcome, in some embodiments, comprises a specific side effect or plurality of side effects relating to a treatment including, for example, nausea, fever, headache, and weight loss. In this manner, an outcome represents a safety of a treatment with regard to side effects related to or resulting from the treatment.

As described, in a hierarchical clustering technique, outcomes are grouped together based on a distance metric. An example of a distance metric that might be set includes a period of time. For example, where an outcome to be clustered comprises a survival rate following the initiation of a treatment, a distance metric comprises, in this exemplary embodiment, a single year. In this example, patients who survived 5 years following treatment initiation may be grouped together because they all survived within the same year (i.e., one year which is the distance metric) from one another following the initiation of treatment. In this example, a group of patients that survived 4 years following treatment initiation may be the nearest group within the hierarchy of groupings because the second group (4 year survival) is just one year (i.e., the distance metric) apart from the first group (5 year survival). A dendrogram of clusters formed using this metric would show these two groups, 5 and 4 year survivals, and their relationships to other groups clustered based on survival from treatment initiation (e.g., a 3 year survival group). It should be understood that other durations are suitable for use with the clustering technique described herein including durations lasting any number of years including, for example, 1, 2, 3, 4, 5, 6, 7, 8, 9, or 10 years, durations lasting any number of months including, for example, 1, 2, 3, 4, 5, 6, 7, 8, 9, 10, 11, or 12 months, durations lasting hours including, for example, 1, 2, 3, 4, 5, 6, 7, 8, 9, 10, 11, 12, 13, 14, 15, 16, 17, 18, 19, 20, 21, 22, 23, or 24 hours.

In another exemplary embodiment, an outcome comprises an efficacy outcome which, in this exemplary embodiment, comprises a survival time following initiation of a treatment. Non-limiting examples of a data metric suitable for use in this exemplary embodiment include pain level following initiation of treatment (e.g., as indicated on a subjective scale), weight gain following initiation of treatment, increased appetite following initiation of treatment (e.g., as indicated on a subjective scale), changes in radiographic data (e.g., a measure of change of tumor size), or changes in vital signs following initiation of treatment.

In another exemplary embodiment, an outcome comprises a safety outcome which, in this exemplary embodiment, comprises side-effects experienced following initiation of a treatment. Non-limiting examples of a data metric suitable for use in this exemplary embodiment include total number of side effects reported, degree of severity of at least one side effect (e.g., as indicated on a subjective scale), degree of weight loss, or degree of loss of productivity (e.g., as measured by number of days absent from work).

In an exemplary embodiment of an insights engine configured to output a prediction regarding an outcome of a patient as described herein, data that is clustered using a hierarchical clustering technique (or any other suitable clustering technique) is divided into individual clusters using a modified gap statistic technique. A gap statistic technique compares intra-cluster variation for different outcomes and a modified gap statistic technique uses intra-cluster variation data to divide the different clusters into smaller numbers of clusters (e.g., individual clusters). In an exemplary next step of a predictive technique that utilizes clustering of individuals or populations of individuals by outcomes as described herein, predictive models are applied to the divided outcome clusters, wherein the outcome clusters are the dependent variables and the full set of patient characteristics are the independent variables. Exemplary predictive models applied to the one or more outcome clusters include Elastic Net Multinomial Regression and Gradient Boosted Machines. Both predictive models, once trained, correctly classify patients into similar outcome clusters with >90% accuracy.

Re-clustering occurs over time, in some embodiments, when new clusters are formed or individual results are moved into new clusters in response to additional data being received. That is, an individual's data originally placed into a first cluster may be moved to a second cluster based on additional data that is received such as, for example, new test results or findings which results in a new (i.e., different) outcome prediction. Similarly, additional data received for one or more individuals may result in a totally new outcome prediction that results in a new cluster containing individuals with the totally new outcome that is predicted. Additional data received may represent changes in existing parameters or new parameters not previously available such as, for example, patient weight, patient age, patient reported pain levels, and patient reported tolerance of treatment. Additional data received may represent changes in existing diagnostic data or new diagnostic data such as, for example, radiographic data, laboratory results, and biopsy result. Additionally, new data used to make new predictions may be in the form of intermediate outcomes. For example, an intermediate outcome may comprise an initial treatment result such as an indication of a remission of a cancer. Other non-limiting examples of intermediate outcomes include onset of side effects, tumor growth or invasion, metastasis, radiation toxicity, decrease in tumor size or degree of invasiveness, and decrease in number of metastases. In general, in such embodiments, as additional parameters related to individuals become available, the additional data is used by the software described herein to run new outcome predictions that may affect how the original data is clustered (i.e., a different or new prediction may be made based on the additional data).

In some of these and other embodiments, an output of a data insights engine is presented to one or more of a healthcare provider, a patient, and/or a third party through one or more interfaces. In some embodiments, an interface as described herein comprises a custom interface.

Interfaces

A platform as described herein typically includes different interface types customized to a specific type of user and of which there may be different numbers within the platform. For example, in some embodiments, a platform comprises healthcare provider application which comprises a healthcare provider interface, a patient application which comprises a patient interface, and a third party application which comprises a third party interface. In some embodiments, each of the healthcare provider interface, patient interface, and third party interface each comprise a custom interface that is respectively customized for a healthcare provider, a patient and a third party.

A platform in some embodiments comprises a healthcare provider application which comprises a healthcare provider interface and a patient application which comprises a patient interface, and wherein each interface is customized to a specific user, i.e., the healthcare provider and patient respectively.

A single platform as described herein may comprise one or more of any type of interface described herein. That is, in some embodiments, for example, a platform comprises a single healthcare provider application, fifty patient applications (each with a different patient/user), and two third party applications (each with a different third party). It should be understood that, in some embodiments, a single application comprises a plurality of interfaces. For example, in the previous example wherein a platform comprises a single healthcare provider application, fifty patient applications (each with a different patient/user), and two third party applications, the single healthcare provider application comprises fifty interfaces, one interface corresponding to each patient/user using a patient application on the platform. Similarly, for example, in an embodiment of a platform including a plurality of healthcare provider applications (each corresponding to a different healthcare provider), a patient application may comprise two or more interfaces, wherein a single interface corresponds to a different healthcare provider using a healthcare provider application on the platform.

In general, various embodiments of interfaces as described herein comprise different components that are configured to present or receive input in different data formats including, for example, graphical formats, audio formats, and video formats.

In some embodiments, an interface comprises one or more portals configured to provide interactive data that, in some embodiments, is customized to a type of user.

In general, a healthcare provider interface in a healthcare provider application is configured to: (1) simplify the complexities involved in providing patient care and (2) integrate patient input into the healthcare provider decision making process. In general, addressing the complexities involved in providing patient care is achieved by providing the data insights engine output to a healthcare provider within the healthcare provider interface. In general, integrating patient input in the decision making process is achieved by providing input provided by a patient within the healthcare provider interface as well as, in some embodiments, providing the patient input to the data insights engine which may result in a particular output from the data insights engine that is based at least in part on the patient input.

Data is typically organized, presented, and/or received in a healthcare provider application, patient application, and/or a third party application within a portal (or a portion of a portal). A portal typically comprises interactive links, images, and/or buttons that allow a user to directly interact with the content that is displayed in the portal. Non-limiting examples of content displayed in a portal includes healthcare provider identifying data, patient identifying data, third party identifying data, patient health data, and output(s) from a data insights engine. In some embodiments, a portal includes a plurality of screens that include different content from one another. In some embodiments, a healthcare provider has a single portal in which he or she is able to access the health data of all of his or her patients. In some embodiments, a healthcare provider has a single portal for each one of his or her patients (i.e., each patient has an individual portal). Likewise, in some embodiments, if a patient is cared for by more than one healthcare provider, he or she has an individual portal for each healthcare provider. Likewise, in some embodiments, a healthcare provider has an individual portal for each third party that he or she interacts with and, in some embodiments, a healthcare provider portal is configured to be used for third party interactions in addition to other functions including patient related functions.

In some embodiments, one or more portals of a custom interface (e.g., healthcare provider interface, patient interface, and/or third party interface) is customized, for example to a specific type of use and/or specific type of data.

In some embodiments, one or more portals of a patient interface of a patient application enable the patient to, for example, obtain physiological data from a sensing device and/or from other health-based software applications, store sensed data from a sensing device, transmit and receive communications, track completion of tasks, and/or transmit physiological, audio, and visual data to a healthcare provider application. In some embodiments of the patient application, the patient application is configured to communicate with another application running within the platform described herein, and, in some embodiments, is also configured to communicate with software applications that are not a part of the platform. In some embodiments, data transmitted to a healthcare provider application from the patient application comprises, for example, height data, weight data, age data, physical activity level data, heart rate data, blood pressure data, and ECG data.

In some embodiments, a patient application is configured to receive a communication from a patient in one or more of written format, audio format, and/or video format. Said communication is inputted into the patient application and the patient is then able to transmit the communication to a healthcare provider application.

In some embodiments, a patient interface is configured to allow a patient to provide feedback (or input) regarding their treatment plan, treatment regimen, and/or treatment goals.

Non-limiting examples of patient feedback (or input) include data regarding symptoms, data regarding side-effects of a treatment, and a change to a previously set goal. For example, a patient may wish to change a treatment goal in view of an upcoming important event. That is, a goal may be to, for example, not have side effects during a marriage of a child scheduled on a specific date. A healthcare provider application in these embodiments, is configured to receive the patient feedback (or input) and where needed adjust accordingly. In the example, of the goal change for the wedding of a family member, a treatment regimen may be, for example, paused or modified in the period leading up to the planned wedding in order to reduce or eliminate the risk of side effects occurring to the patient during the wedding.

A healthcare provider interface, in some embodiments, is configured to receive and display patient data, communications, and feedback (or input). Non-limiting examples of patient data are height, weight, body mass index (BMI), age, physical activity level, heart rate, blood pressure, temperature, and/or ECG data. Non-limiting examples of patient communications include written, audio, and video recorded communications. Non-limiting examples of feedback include feedback (or input) regarding symptoms, side effects, and goals.

The healthcare provider interface may alert the healthcare provider if certain data, communications, and/or feedback is received. For example, an interface of the healthcare provider's software interface may show a list of notifications displaying data such as the patient's communication. In some embodiments, a notification may indicate the receipt of feedback from the patient. In some embodiments, a healthcare provider is able to configure the healthcare provider interface to provide a notification when certain data, communication, and/or feedback is received. For example, if a patient provides feedback that they are experiencing chest pain, a notification may be configured to sound an auditory alarm once the communication is received by the healthcare provider interface. A healthcare provider interface, in some embodiments, may also be configured to issue automated responses to received data, communication, and/or feedback from a patient. For example, an automated response may solicit more data from the patient, may direct the patient to carry out an activity, or may congratulate the patient for achieving a certain task or goal indicated by the received data, communication, and/or feedback. Automated communications to a patient, in some embodiments, may also be configured to be regularly sent (including not in response to any received communication). In these embodiments, an automated communication from a healthcare provider to a patient may be configured to solicit feedback from the patient regarding the treatment regimen that they are receiving.

In some embodiments, a healthcare provider's interface may comprise a viewable, interactive patient directory and/or database. The patient directory and/or database may comprise a list of all patients receiving care from the healthcare provider. The patient directory may further display patient data such as name, phone number, age, gender, and an indication of whether or not they are using the patient interface. Such interface component may be placed in close proximity to the patient's name (or patient image) for ease of accessibility. The healthcare provider interface of the healthcare provider interface may also comprise a component to provide the healthcare provider with the option to add a new patient.

In some embodiments, a third party interface is a part of the platform, wherein non-limiting examples of third parties with a third party interface include healthcare payers, pharmaceutical developers, medical device developers, research institutions, and hospitals. In some embodiments, a third party interface receives health data relating to patients receiving treatment. In some embodiments, a third party interface receives an output from a data insights engine. Said output may, for example, relate to an effectiveness of a treatment regimen or component thereof. The data provided to a third party interface, in some embodiments, is determined by a healthcare provider in the healthcare provider interface.

In general, each interface described herein is configured to communicate with a data insights engine. In some embodiments, each portal within an interface is configured to receive data from or transmit data to (or both) to a data insights engine as described herein. In some embodiments, data to be transmitted to or received from (or both) a data insights engine is/are directly via portal without being initiated by a user, whereas, in some embodiments, data transmission or data receipt (or both) from a data insights engine must be initiated by an action of a user, such as, for example, activating a hyperlink or voice command.

Exemplary Embodiment (a) General Structure

FIG. 1 shows a schematic representation of the architecture and organization of an exemplary embodiment of a platform as described herein. In this embodiment, the platform shown comprises three custom interfaces, each of which is respectively part of a custom application. The interfaces shown in the platform embodiment of FIG. 1 comprise a Healthcare Provider Interface 102, a Patient Interface 104, and a Payer Interface 106.

The platform shown further comprises a Data Insights Engine 100.

Healthcare provider interface 102, Patient Interface 104, and Payer Interface 106, are each components of applications configured to operate on a computing device.

In some embodiments, one or more of interfaces 102, 104, and 106 may be viewed on a computing device. In some embodiments, one or more of interfaces 102, 104, and 106 are viewable on the same computing device containing a Data Insights Engine 100.

While FIG. 1 illustrates a single Healthcare Provider Interface 102, a single Patient Interface 104, a single Payer Interface 106, and a single Data Insights Engine 100, it should be understood that other embodiments of the platform described herein comprise two or more of any of the interfaces 102, 104, and 106 and the Data Insights Engine 100.

In general, each of interfaces 102, 104, and 106 are configured so that a user using the interface is able to interact with data that is provided to him or her via the respective interface (i.e., one of interfaces 102, 104, and 106). That is, in each of interfaces 102, 104, and 106, a user is able to, for example, receive data through, for example, audio, video and/or haptic transmission and a user is able to, for example, transmit to (or enter) data into the respective interface (i.e., one of interfaces 102, 104, and 106) through voice, video and/or touch (including typing on, for example, a touch screen or keyboard).

In some embodiments, a Healthcare Provider Interface 102, a Patient Interface 104, and a Payer Interface 106 all communicate with the Data Insights Engine 100 and receive communications from the Data Insights Engine 100, wherein channels of communication are respectively represented by lines 170, 172, and, 174. In some embodiments, channels of communication 170, 172, and, 174 are two way channels wherein each of the connected interfaces 102, 104, and 106 both transmits to the Data Insights Engine 100 and receives data from the Data Insights Engine 100. In some embodiments, one or more of the communication channels 102, 104, and 106 are a one way channel wherein, for example, one or more of interfaces 102, 104, and 106 receives data from the Data Insights Engine 100 but does not transmit data to the Data Insights Engine 100. Similarly, in some embodiments, for example, one or more of interfaces 102, 104, and 106 transmits data to the Data Insights Engine 100 but does not receive data from the Data Insights Engine 100. Communication channels 102, 104, and 106 comprise any suitable channel for communication between one or more applications including a wired or wireless network, wireless communication not through a network, a hardwired connection, as well as communication through a single computing device (i.e., where, for example, a Data Insights Engine 100 and one or more of interfaces 102, 104, and 106 are located on a single computing device.

While not shown in FIG. 1, in some embodiments of the platform described herein, two or more of interfaces 102, 104, and 106 are able to communicate with one another. That is, it should be understood that in some embodiments, including embodiments including two or more of any of the interfaces 102, 104, and 106 and the Data Insights Engine 100, any of these platform components are configured to communicate with any other of these components either through one way or two way communication. In some embodiments, a communication is initiated or carried out by a user and in some embodiments, a communication is automatically generated. A communication may be in the form of, for example, data, a personal message and/or computer instructions.

A Healthcare Provider Interface 102 is configured to assist a healthcare provider in treating a patient. In some embodiments, a Healthcare Provider Interface 102 provides a portal for a healthcare provider such as, for example, an oncologist to interact with data relating to a plurality of patients which, in some embodiments, comprises patients that are under the care of the healthcare provider.

In some embodiments, one or more custom portals allow a healthcare provider to interact with data and data relating to a plurality of patients comprising patients that are not under the care of the healthcare provider.

(b) Data Groupings and Sub-Groupings

In the embodiment of the platform of FIG. 1 within each of interfaces 102, 104, and 106 data is organized into groupings 108, 110, and 112 and sub-groupings 114, 116, 118, 120, 122, 124, 126, 128, 130, 132, 134, 136, 138, 140, 142, 144, 146, 148, 150, 152, 154, 156, 168, 160, 162, 164, 166, and 168.

As shown, each grouping of data 108, 110, and 112 and sub-grouping of data 114, 116, 118, 120, 122, 124, 126, 128, 130, 132, 134, 136, 138, 140, 142, 144, 146, 148, 150, 152, 154, 156, 168, 160, 162, 164, 166, and 168 may have a title or name within the platform architecture.

It should be understood that data may be organized in various different groupings or sub-groupings in different embodiments of the platforms described herein that may, for example, comprise the same number of groupings and sub-groupings or a different number of groupings and sub-groupings as the platform of FIG. 1. That is, it should be understood that the organization of data described in the following exemplary embodiment is no way intended to be limiting but is provided rather by way of example. For example, in some embodiments data may be organized differently, contain different data than in the example given here, have different titles for the groupings and subgroupings described, and have more or less groupings and subgroupings described.

Any grouping or sub-grouping of data described herein may also include data provided by a Data Insights Engine 100 and/or have, for example, hyperlinks (including both text and image), folders, and/or menus that allow a healthcare provider to interact with the Data Insights Engine 100 from within a portal for any general grouping or sub-grouping of data.

In general, a single general grouping or a single sub-grouping of data may each correspond to a single portal within an interface 102, 104, and 106 or may be a part of a portal that includes other data not within the same grouping or sub-grouping.

(c) Healthcare Provider Interface

Within some embodiments of the Healthcare Provider Interface 102, data is generally organized into three groupings as shown in FIG. 1, which may be accessed and expanded through, for example, hyperlinks (including both text and image), folders, and/or menus within the Healthcare Provider Interface 102. The three general groupings in which data is organized in some embodiments of the platform comprise the groupings of Patient Context 108, Outcome Navigator 110, and Clinical Actions 112.

In some embodiments, within the grouping of Patient Context 108 are the following exemplary sub-groupings of data: Patient Overview 114, Cancer Timeline 116, Disease Context: Labs/Tumor Markers 118, Disease Context: Imaging 120, Medical History/Encounters 122, and Patient Status 124. The Patient Context 108 grouping, in some embodiments, comprises a portal dedicated to that grouping and, in some embodiments, comprises a portion of a portal shared with other data. Similar to the groupings 108, 110, and 112, in some embodiments of the platform, the sub-groupings 114, 116, 118, 120, 122, and 124 may be accessed and expanded through, for example, hyperlinks (including text and images), folders, and/or menus within the interface.

Figure 2:
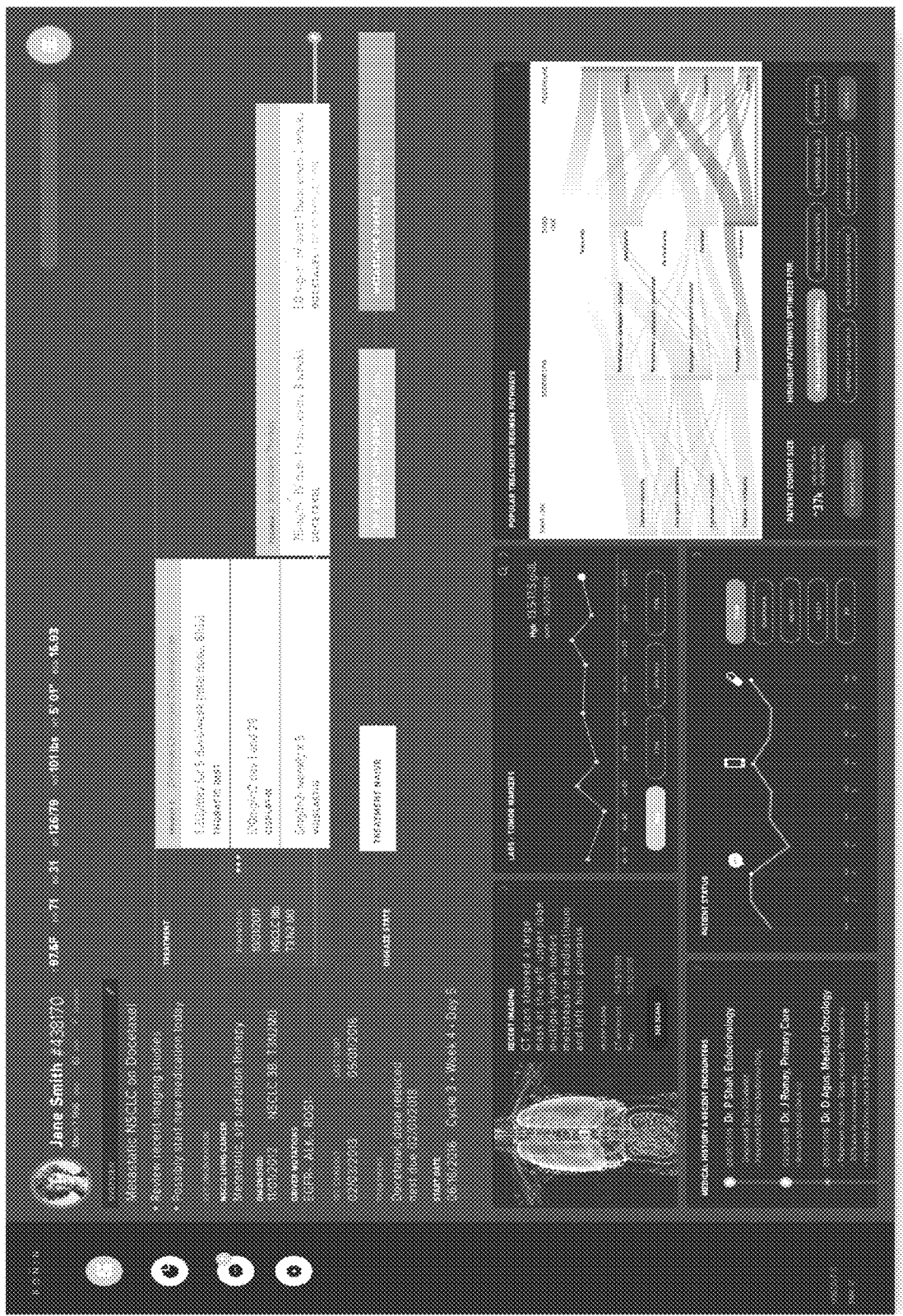
FIG. 2 shows an exemplary portal of a Healthcare Provider Interface that comprises an exemplary Patient Overview data sub-grouping.

In some embodiments, a Patient Overview data sub-grouping 114 comprises data that provides a snapshot of a patient including, for example, their demographic data, their diagnosis, a photo or other representation of the patient of the healthcare provider using the Healthcare Provider Interface 102 (e.g., an avatar), and their treatment regimen. Generally, the data within the Patient Overview 114 is succinct and presented in a short easy to scan format so that a healthcare provider is able to quickly orient to the patient for whom the data is provided. In some embodiments, a Patient Overview data sub-grouping 114 comprises a portal dedicated to that sub-grouping and, in some embodiments, comprises a portion of a portal shared with other data. FIG. 2 shows an exemplary portal of a Healthcare Provider Interface 102 that comprises an exemplary Patient Overview data sub-grouping 114 comprising a graphical user interface having a patient name, image, and demographic information shown at the top and top left of the portal.

In some embodiments, a Cancer Timeline data sub-grouping 116 provides a representation of the timeline of a patient's care. In some embodiments, a Cancer Timeline data sub-grouping 116 comprises a visual representation of data. In some embodiments, a Cancer Timeline data sub-grouping 116 comprises an interactive visual representation of data including, for example, hyperlinks (including text and images), folders, and/or menus. In some embodiments, a Cancer Timeline data sub-grouping 116 comprises a portal dedicated to that sub-grouping and, in some embodiments, comprises a portion of a portal shared with other data. As shown, the portal of FIG. 2 shows a Cancer Timeline data sub-grouping 116 in the middle and bottom of the portal.

In some embodiments, a Disease Context: Labs/Tumor Markers data sub-grouping 118 provides data regarding the nature of a patient's cancer. For example, tumor marker levels from a sample taken from a patient. Non-limiting examples of samples include blood, serous fluid, tissue (e.g., from biopsy), urine, and CSF. In some embodiments, Disease Context: Labs/Tumor Markers data sub-grouping 118 provides staging data relating to the patient of the healthcare provider using the Healthcare Provider Interface 102. In some embodiments, a Disease Context: Labs/Tumor Markers data sub-grouping 118 also includes lab values from before the patient of the healthcare provider using the Healthcare Provider Interface 102 was diagnosed with cancer. In some embodiments, a Disease Context: Labs/Tumor Markers data sub-grouping 118 comprises a portal dedicated to that sub-grouping and, in some embodiments, comprises a portion of a portal shared with other data. A Disease Context: Labs/Tumor Markers data sub-grouping 118 is shown in the middle of FIG. 2.

In some embodiments, a Disease Context: Imaging data sub-grouping 120 provides radiographic images for the patient of the healthcare provider using the Healthcare Provider Interface 102. Non-limiting examples of images include X-ray, Ultrasound, Nuclear Scan, CT, MM, Cystogram, ERCP, and angiography. In some embodiments, a Disease Context: Imaging data sub-grouping 120 also includes radiologist interpretations and procedure notes. In some embodiments, a Disease Context: Imaging data sub-grouping 120 comprises a portal dedicated to that sub-grouping and, in some embodiments, comprises a portion of a portal shared with other data. A Disease Context: Imaging data sub-grouping 120 is shown in the middle left of FIG. 2.

In some embodiments, a Medical History/Encounters data sub-grouping 122 provides a summary of the prior medical history and healthcare encounters of a patient. In some embodiments, a Medical History/Encounters data sub-grouping 122 comprises a portal dedicated to that sub-grouping and, in some embodiments, comprises a portion of a portal shared with other data. A Medical History/Encounters data sub-grouping 122 is shown in the bottom left of FIG. 2.

In some embodiments, a Patient Status data sub-grouping 124 provides a summary of the current status of the patient of the healthcare provider using the Healthcare Provider Interface 102. In some embodiments, a Patient Status data sub-grouping 124 comprises a portal dedicated to that grouping and, in some embodiments, comprises a portion of a portal shared with other data.

In some embodiments, within the general data grouping of Outcome Navigator 110 are the following exemplary sub-groupings of data: Cohort Definition 126, Pathway Navigator 128, Treatment Explorer/Treatment Comparison 130, Aggregated Data 132, Published Data 134, Expert Tips 136, Algorithms/Institutional Knowledge 138, Patient Shared Decision-Making 140, and Supportive Care 142. The Outcome Navigator 110 grouping, in some embodiments, comprises a portal dedicated to that grouping and, in some embodiments, comprises a portion of a portal shared with other data. Similar to the groupings 108, 110, and 112, in some embodiments of the platform, the sub-groupings 126, 128, 130, 132, 134, 136, 138, 140, and 142 may be accessed and expanded through, for example, hyperlinks (including text and images), folders, and/or menus within the interface.

Figure 3:
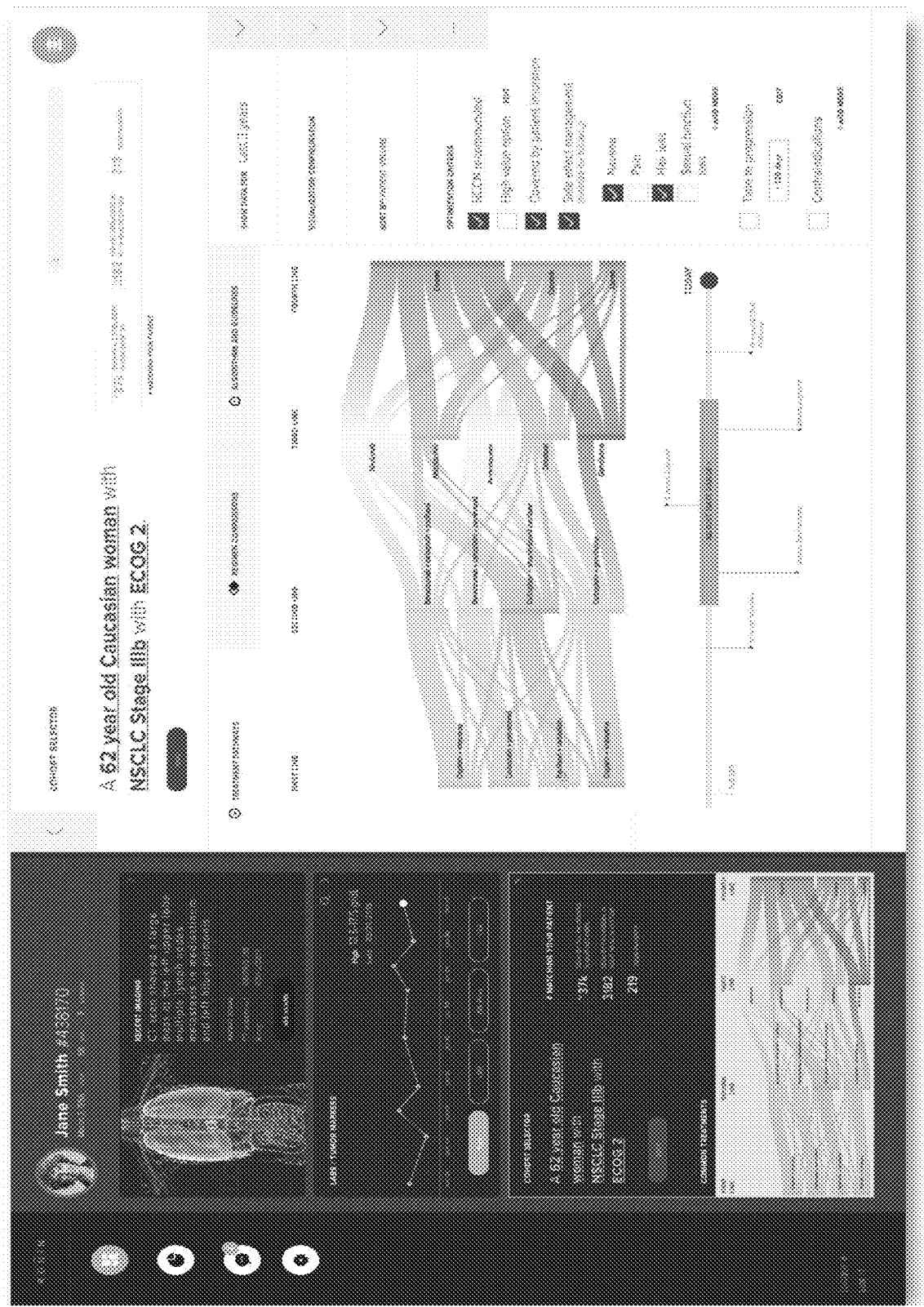
FIG. 3 shows an exemplary portal of a Healthcare Provider Interface showing a Cohort Definition data sub-grouping.

In some embodiments, a Cohort Definition data sub-grouping 126 provides data regarding one or more similarly situated patients. For example, a Cohort Definition data sub-grouping 126 may comprise a portal that provides a means for a healthcare provider to enter data (including, for example, via voice and via text) and the Data Insights Engine 100 identifies a similarly situated patient to the patient of the healthcare provider using the Healthcare Provider Interface 102 based on the data entered by the healthcare provider. Generally, a Cohort Definition data sub-grouping 126 receives data regarding similarly situated patients to the patient of the healthcare provider using the Healthcare Provider Interface 102 based on data from medical records including, for example, data received from one or EMRs. In some embodiments, once one or more similarly situated patients are identified in the Cohort Definition data sub-grouping 126, their respective treatment plans, treatment regimens, and/or treatment goals including outcomes are provided including, in some embodiments, outcomes for any one step of a treatment regimen. In some embodiments, a Cohort Definition data sub-grouping 126 comprises a portal dedicated to that sub-grouping and, in some embodiments, comprises a portion of a portal shared with other data. A Cohort Definition data sub-grouping 126 is shown in the bottom right of the portal of FIG. 2. FIG. 3 shows an exemplary portal of a Healthcare Provider Interface 102 showing a Cohort Definition data sub-grouping. A larger/expanded version of a Cohort Definition data sub-grouping 126 is shown on the right side of the portal of FIG. 3.

In some embodiments, a Pathway Navigator data sub-grouping 128 provides data regarding one or more treatment plans, treatment regimens, and/or treatment goals in an interactive visual format. For example, a Pathway Navigator data sub-grouping 128, in some embodiments, provides a timeline of a treatment plan, treatment regimen, and/or treatment goals and, in some embodiments, incorporates interactive images or hyperlinks. The timeline can include first line, second line, third line, fourth line, etc., treatment in the case of cancer. In some embodiments, a Pathway Navigator data sub-grouping 128 comprises a portal dedicated to that sub-grouping and, in some embodiments, comprises a portion of a portal shared with other data. A Pathway Navigator data sub-grouping 128 is shown on the right side of the portals shown in FIGS. 2 and 3. The portal for the Pathway Navigator data sub-grouping 128 can include one or more interactive controls for sorting (e.g., limiting data to a certain time-frame or sorting by patient volume), optimization criteria (e.g., NCCN recommended, high value option, covered by patient insurance, side effect management, or time to progression). Various side effects can include nausea, pain, hair loss, sexual dysfunction or function loss, and other known side effects. The portal may show a timeline for the approval of certain therapies and/or when relevant data became known or published (e.g., clinical trial results for a particular therapy is published). The portal may include selectable options for one or more of showing treatment pathways, regimen comparisons, and algorithms and/or guidelines.

Figure 4:
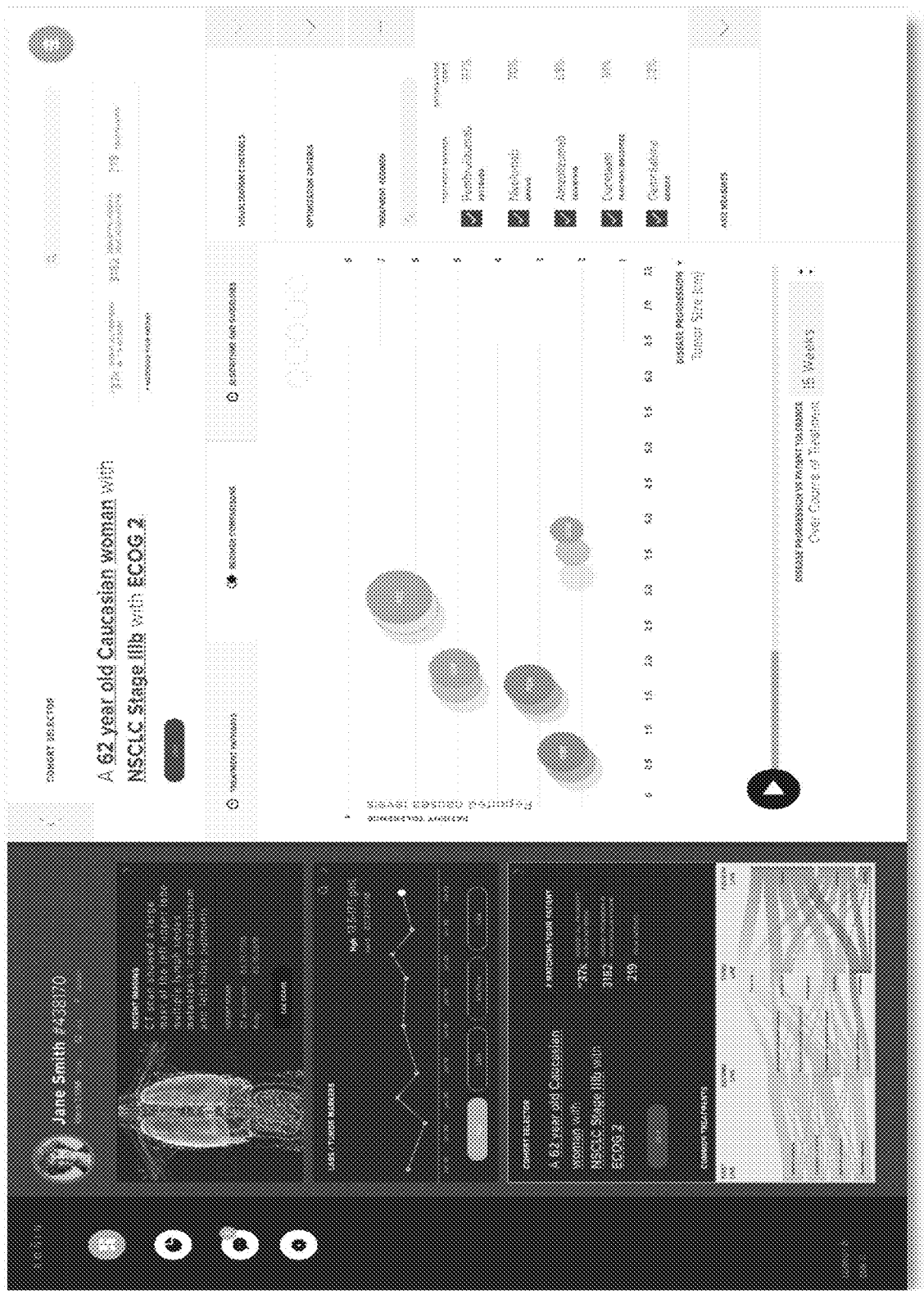
FIG. 4 shows an exemplary portal of a Healthcare Provider Interface showing a Treatment Explorer/Treatment Comparison data sub-grouping.

In some embodiments, a Treatment Explorer/Treatment Comparison data sub-grouping 130 provides data regarding one or more treatment plans, treatment regimens, and/or treatment goals in an interactive format wherein treatment plans, treatment regimens, and/or treatment goals of similarly situated patients may be further analyzed or compared by a healthcare provider. In some embodiments, a Treatment Explorer/Treatment Comparison data sub-grouping 130 comprises a portal dedicated to that sub-grouping and, in some embodiments, comprises a portion of a portal shared with other data. FIG. 4 shows an exemplary portal of a Healthcare Provider Interface 102. A Treatment Explorer/ Treatment Comparison data sub-grouping 130 is shown on the right of the portal of FIG. 4 which in this example shows data relating to disease progression vs. patient tolerance.

In some embodiments, an Aggregated Data data sub-grouping 132 provides data regarding one or more treatment plans, treatment regimens, and/or treatment goals in the form of aggregated data. In some embodiments, the aggregated data within the Aggregated Data data sub-grouping 132 is ingested and/or aggregated by the Data Insights Engine 100 In some embodiments, an Aggregated Data data sub-grouping 132 comprises a portal dedicated to that sub-grouping and, in some embodiments, comprises a portion of a portal shared with other data.

In some embodiments, a Published Data sub-grouping 134 provides data regarding one or more treatment plans, treatment regimens, and/or treatment goals in the form of published data. In some embodiments, a Published Data sub-grouping 134 comprises a portal dedicated to that sub-grouping and, in some embodiments, comprises a portion of a portal shared with other data.

In some embodiments, an Expert Tips data sub-grouping 136 provides data regarding one or more treatment plans, treatment regimens, and/or treatment goals in the form of suggestions from experts in the field. In some embodiments, an Expert Tips data sub-grouping 136 comprises a portal dedicated to that sub-grouping and, in some embodiments, comprises a portion of a portal shared with other data. The Expert Tips data can be obtained from various guidelines available, for example, treatment recommendations for a particular cancer type and stage such as the National Comprehensive Cancer Network (NCCN) guidelines for treatment of cancer.

In some embodiments, an Algorithms/Institutional Knowledge data sub-grouping 138 provides data regarding one or more treatment plans, treatment regimens, and/or treatment goals in the form of an algorithm or institutional knowledge. In some embodiments, an Algorithms/Institutional Knowledge data sub-grouping 138 provides a healthcare provider with treatment protocols established in the field or in an institution in which a healthcare provider provides care. In some embodiments, an Algorithms/Institutional Knowledge data sub-grouping 138 comprises a portal dedicated to that sub-grouping and, in some embodiments, comprises a portion of a portal shared with other data.

In some embodiments, a Patient Shared Decision-Making data sub-grouping 140 provides data regarding, for example, the feedback, request, and/or expressed needs of various patients who were treated for a medical condition such as, for example, a cancer. In some embodiments, the patient data Patient Shared Decision-Making data sub-grouping 140 is from patients who shared one or more of their treatment plan, their treatment regimen, and/or treatment goals with the patient of the healthcare provider who is using the Healthcare Provider Interface 102. In some embodiments, a healthcare provider is provided with a suggestion for how to optimally address the feedback, request, and/or expressed need relating to one or more of their treatment plan, their treatment regimen, and/or treatment goals of his or her patients based on the information provided by other patients. In some embodiments, a Patient Shared Decision-Making data sub-grouping 140 comprises a portal dedicated to that sub-grouping and, in some embodiments, comprises a portion of a portal shared with other data.

In some embodiments, a Supportive Care data sub-grouping 142 provides data regarding one or more options for providing care that support or supplement one or more of the treatment plan, treatment regimen or treatment goals. Non-limiting examples of supportive care include nutritional care, physical therapy, nursing assistance, speech therapy, social work, and mental health/counseling services. In some embodiments, a Supportive Care data sub-grouping 142 comprises a portal dedicated to that sub-grouping and, in some embodiments, comprises a portion of a portal shared with other data.

In some embodiments, within the general grouping of Clinical Actions 112 are the following exemplary sub-groupings of data: Orders 144, Smart Authority 146, Notes 148, Patient Engagement 150, Outcomes 162, Cost/Reimbursement 164, Patient Satisfaction 166, and Data Contribution/Superuser 168. The Clinical Actions 112 grouping, in some embodiments, comprises a portal dedicated to that grouping and, in some embodiments, comprises a portion of a portal shared with other data. Similar to the groupings 108, 110, and 112, in some embodiments of the platform, the sub-groupings 144, 146, 148, 150, 162, 164, 166, and 168 may be accessed and expanded through, for example, hyperlinks (including text and images), folders, and/or menus within the interface.

In some embodiments, an Orders data sub-grouping 144 provides a portal (or portion of a portal) directed to a healthcare provider's orders relating to his or her patients. For example, Orders 144 may comprise a portal that provides a means for a healthcare provider to enter orders to be carried out for one or more of his or her patients (including order in the form of, for example, via voice and via text). In some embodiments, an Orders data sub-grouping 144 stores previous orders placed by the healthcare provider for one or more of his or her patients. In some embodiments, an Orders data sub-grouping 144 is configured to provide a healthcare provider an analysis of his or her orders carried out by the Data Insights Engine 100. For example, in some embodiments, a data Insights Engine 100 may provide data to a healthcare provider that allows the healthcare provider to compare his order or previous orders to orders placed by other healthcare providers. In some of these embodiments, the Data Insights Engine 100 determines what data regarding orders is most relevant or useful to the particular healthcare provider who is using the healthcare provider interface 108. In some embodiments, once one or more similarly situated patients or healthcare providers are identified by the Data Insights Engine 100, and their respective orders including outcomes are provided within the Orders data sub-grouping 144 including, in some embodiments, outcomes for any one step order. In some embodiments, an Orders data sub-grouping 144 comprises a portal dedicated to that grouping and, in some embodiments, comprises a portion of a portal shared with other data.

In some embodiments, a Smart Authority data sub-grouping 146 provides data in the form of, for example, an accepted study or textbook relating to a care of one or more patients of a healthcare provider using the Healthcare Provider Interface 108. For example, a Smart Authority data subgrouping 146, in some embodiments, provides data relating to a treatment plan, treatment regimen, and/or treatment goal of a patient. In some embodiments, a Smart Authority data sub-grouping 146 is configured to provide a healthcare provider data from an accepted study or textbook selected by the Data Insights Engine 100. For example, in some embodiments, a data Insights Engine 100 determines what data from a study or textbook is most relevant or useful to the particular healthcare provider who is using the healthcare provider interface 108. In some embodiments, once one or more studies or textbooks are identified by the Data Insights Engine 100, the healthcare provider is provided an algorithm or outcomes relevant to the treatment of one or more patients of the healthcare provider using the Healthcare Provider Interface 108. In some embodiments, a Smart Authority data sub-grouping 146 comprises a portal dedicated to that sub-grouping and, in some embodiments, comprises a portion of a portal shared with other data.

In some embodiments, a Notes data sub-grouping 148 provides a portal (or portion of a portal) directed to a healthcare provider's notes relating to his or her patients. For example, a Notes data sub-grouping 148 may comprise a portal that provides a means for a healthcare provider to enter orders to be carried out for one or more of his or her patients (including in the form of, for example, voice and text). In some embodiments, a Smart Authority data sub-grouping 146 comprises a portal dedicated to that sub-grouping and, in some embodiments, comprises a portion of a portal shared with other data.

In some embodiments, a Patient Engagement data sub-grouping 150 provides data regarding patient feedback regarding one or more treatment plans, treatment regimens, and/or treatment goals. For example, in some embodiments, feedback is received from a patient being treating by the healthcare provider who is using the Healthcare Provider Interface 108. In some embodiments, feedback presented in a Patient Engagement data sub-grouping 150 is received from a Patient Interface 104. In some embodiments, a Patient Engagement data sub-grouping 150 comprises a portal (or portion of a portal) configured to integrate patient feedback into one or more of a treatment plan, treatment regimen, and/or treatment goal of the patient. In some embodiments, Patient Engagement data sub-grouping 150 is raw verbatim feedback only. In some embodiments, Patient Engagement data sub-grouping 150 presents a course of action that will address the received patient feedback. For example, in some embodiments, a data Insights Engine 100 analyzes the feedback provided by the patient, determines one or more actions that address the patient feedback, and presents the one or more actions within the Patient Engagement data sub-grouping 150. In some embodiments, after analyzing patient feedback, a data Insights Engine 100 may be configured to clean the received feedback data in terms of, for example, typographical errors or other inadvertently entered incorrect information. In some embodiments, after analyzing patient feedback, a Data Insights Engine 100 may generate and transmit one or more questions to a Patient Interface 108 in order to, for example, obtain additional data from the patient. In some embodiments, a Patient Interface 108 is dedicated to that sub-grouping and, in some embodiments, comprises a portion of a portal shared with other data.

Figure 5:
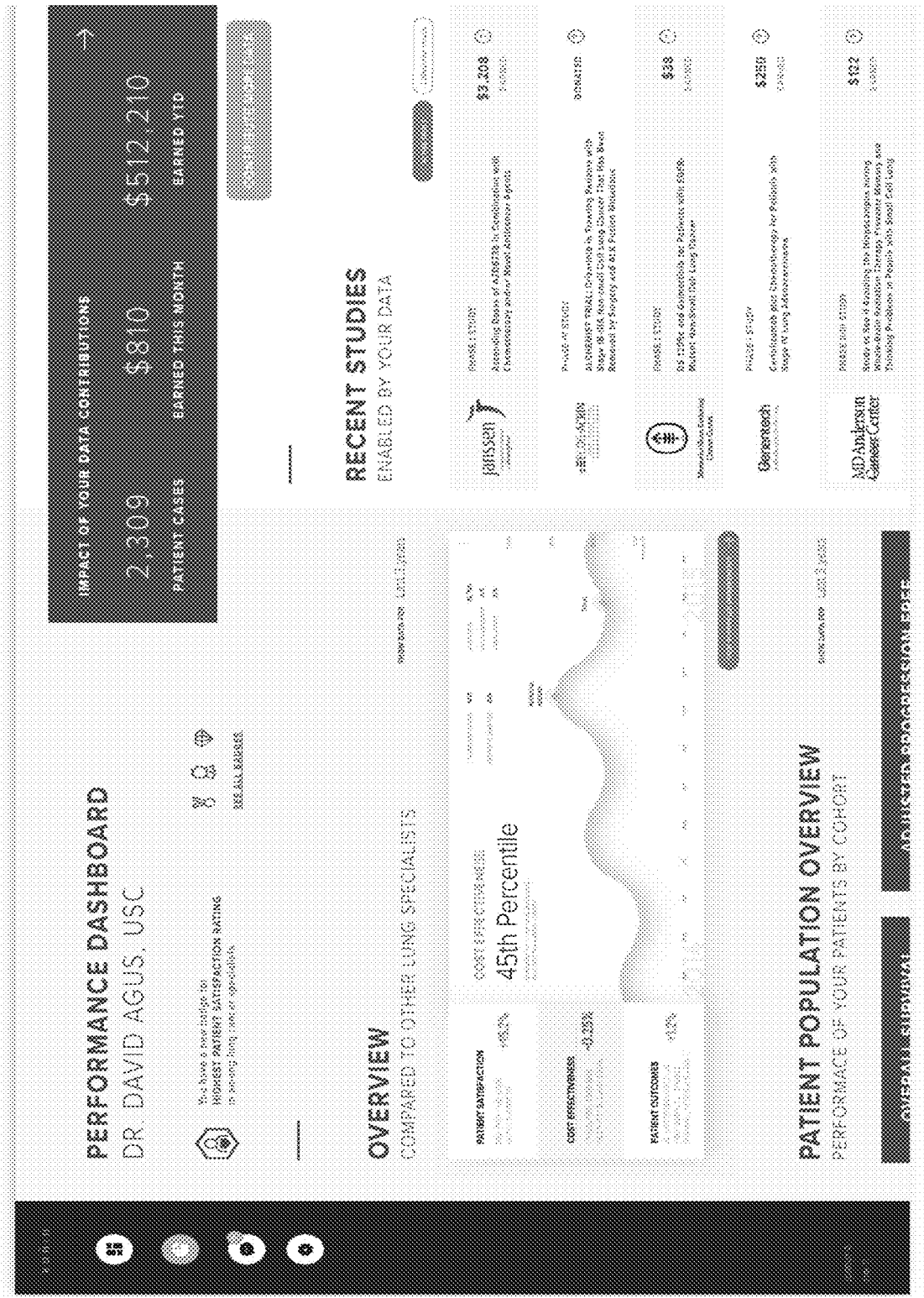
FIG. 5 shows an exemplary portal of a Healthcare Provider Interface showing a graphic presenting performance of healthcare providers.

In some embodiments, an Outcomes data sub-grouping 162 comprises a portal (or portion of a portal) directed to a healthcare provider's outcomes relating to his or her patients. In some embodiments, an outcome presented in the Outcomes data sub-grouping 162 is presented with respect to one or more treatment plans, treatment regimens, and/or treatment goals. In some embodiments, one or more outcomes of one or more patients of the healthcare provider who is using the Healthcare Provider Interface 108 are compared to other outcomes. In some embodiments, one or more outcomes of one or more patients of the healthcare provider who is using the Healthcare Provider Interface 108 are compared to a previous outcome of one or more patient of the healthcare provider who is using the Healthcare Provider Interface 108. In some embodiments, one or more outcomes of one or more patients of the healthcare provider who is using the Healthcare Provider Interface 108 are compared to an outcome of a different healthcare provider. FIG. 5 shows an exemplary portal of a Healthcare Provider Interface 102. FIG. 5 shows a graphic presenting performance of other healthcare providers and in this particular example shows the performance of the healthcare provider who is using the Healthcare Provider Interface 108 as compared to the performance of other healthcare providers. In the example of FIG. 5 it is determined that the performance of the healthcare provider who is using the Healthcare Provider Interface 108 places him or her within the $45^{nd}$ percentile with respect to the other healthcare providers. In some embodiments, a data Insights Engine 100 provides an analysis of a healthcare provider performance with respect to, for example, patient satisfaction, cost effectiveness, and patient outcomes and presents examples of ways in which one or more other healthcare providers achieved improved outcomes. In some embodiments, an Outcomes data sub-grouping 162 comprises a portal dedicated to that grouping and, in some embodiments, comprises a portion of a portal shared with other data.

Figure 6:
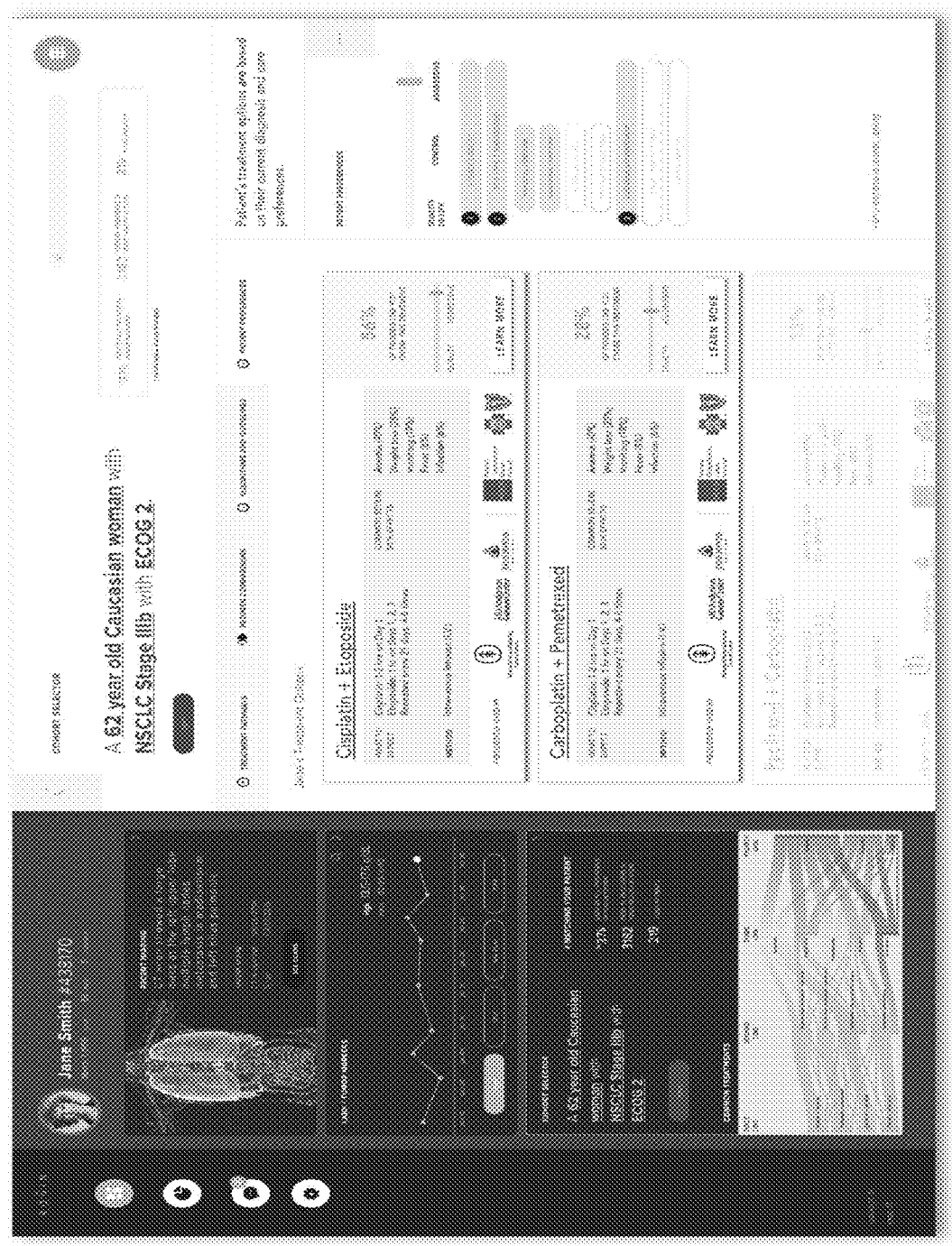
FIG. 6 shows an exemplary portal of a Healthcare Provider Interface that includes financial data.

In some embodiments, a Cost/Reimbursement data sub-grouping 164 provides data regarding the financials relating to a treatment of one or more patients of a healthcare provider who is using the Healthcare Provider Interface 108. In some embodiments, the financial information presented in the Cost/Reimbursement data sub-grouping 164 is presented with respect to one or more treatment plans, treatment regimens, and/or treatment goals with which the financials are associated. In some embodiments, a Cost/Reimbursement data sub-grouping 164 provides information that assists a healthcare provider in making decisions relating to healthcare payers and reimbursement. FIG. 6 shows an exemplary portal of a Healthcare Provider Interface 102 that includes financial data. FIG. 6 shows one or more aspects of a treatment regimen along with payer information for payers who reimburse the particular treatment regimen aspect. In some embodiments, a Cost/Reimbursement data sub-grouping 164 comprises a portal dedicated to that sub-grouping and, in some embodiments, comprises a portion of a portal shared with other data.

In some embodiments, a Patient Satisfaction data sub-grouping 166 provides data regarding a satisfaction of a patient with one or more treatment plans, treatment regimens, and/or treatment goals. In some embodiments, a data Insights Engine 100 determines a satisfaction level based on feedback received from one or more patients through a Patient Interface 104. In some embodiments, a Patient Satisfaction data-subgrouping 166 provides a suggestion from a data Insights Engine 100 as to how to take an action that will improve the satisfaction of one or more patients of healthcare provider who is using the Healthcare Provider Interface 108. In some embodiments, a Patient Satisfaction data-subgrouping 166 comprises a portal dedicated to that grouping and, in some embodiments, comprises a portion of a portal shared with other data.

In some embodiments, a Data Contribution/Superuser data sub-grouping 168 provides data regarding the data that is presented in one or more portals of a Healthcare Provider Interface 108 typically where the data relates to one or more treatment plans, treatment regimens, and/or treatment goals. In some embodiments, a Data Contribution/Superuser data sub-grouping 168 provides a means for a user (or administrator) to track, analyze, and/or modify how data is presented within a Healthcare Provider Interface 108. In some embodiments, a Data Contribution/Superuser data sub-grouping 168 comprises a portal dedicated to that sub-grouping and, in some embodiments, comprises a portion of a portal shared with other data.

(d) Patient Interface

A Patient Interface 104 is configured to provide a patient with an interactive tool for interacting with a healthcare provider in a manner that assists the healthcare provider in administering the care to the patient. In some embodiments, a Patient Interface 104 provides one or more portal for a patient to be able to review and interact with data relating to one or more of a treatment plan, treatment regimen, and/or treatment goal. Data in a Patient Interface 104, in some embodiments, is presented within: an Education/Visualizations data sub-grouping 152 and a Patient Relationship Management (e.g. CRM—PROs (Chatbots)) data sub-grouping 154. It should be understood, however, that the organization of data described in the following exemplary embodiment(s) is no way intended to be limiting but is provided rather by way of example. For example, in some embodiments data may be organized differently, contain different data than in the example given here, have different titles for the groupings and sub-groupings described, and have more or less groupings and sub-groupings described. Any grouping or sub-grouping in embodiments of the platform described herein may also include data provided by Data Insights Engine 100 and/or have, for example, hyperlinks (including both text and image), folders, and/or menus that allow a healthcare provider to interact with the Data Insights Engine 100 from within the portal for any grouping or sub-grouping of a platform.

In some embodiments, an Education Visualization data sub-grouping 152 provides data regarding one or more treatment plans, treatment regimens, and/or treatment goals in the form of educational information in the format of one or both of text or video formats. In some embodiments, an Education Visualization data sub-grouping 152 comprises a portal dedicated to that sub-grouping and, in some embodiments, comprises a portion of a portal shared with other data.

In some embodiments, a Patient Relationship Management data sub-grouping 154 provides a portal (or portion of a portal) configured to enhance a patient interaction with a healthcare provider and provide means for communicating feedback to a healthcare provider. In some embodiments, feedback is provided by the patient in response to an inquiry transmitted to a patient by a healthcare provider or automatically generated by the platform. In some embodiments, a data Insights Engine 100 generates an inquiry that is transmitted to the patient to solicit specific feedback. In some embodiments, automatically generated inquiries are transmitted to the patient via a "bot" or an automated messaging application. In some embodiments, feedback provided by a patient through a Patient Relationship Management data sub-grouping 154 is received by a data Insights Engine 100 and used as described herein to assist in the decision making of a healthcare provider in order to enhance the treatment of the patient and other similarly situated patients. In some embodiments, Patient Relationship Management 154 comprises a portal dedicated to that grouping and, in some embodiments, comprises a portion of a portal shared with other data.

(e) Payer Interface

A Third Party Interface 106 is configured to provide an interactive interface for a third party such as, for example a payer or pharmaceutical developer or medical device developer to interact with data provided by healthcare providers and patients within the exemplary platform of FIG. 1. Data in a Payer Interface 106, in some embodiments, is presented within: a Network Performance data sub-grouping 156, a Network Outcomes data sub-grouping 158, and a Pathway Management 160 data sub-grouping 154. It should be understood, however, that the organization of data described in the following exemplary embodiment(s) is no way intended to be limiting but is provided rather by way of example. For example, in some embodiments data may be organized differently, contain different data than in the example given here, have different titles for the groupings and sub-groupings described, and have more or less groupings and sub-groupings described. Any grouping or sub-grouping in embodiments of the platform described herein may also include data provided by Data Insights Engine 100 and/or have, for example, hyperlinks (including both text and image), folders, and/or menus that allow a healthcare provider to interact with the Data Insights Engine 100 from within the portal for any grouping or sub-grouping of a platform.

In some embodiments, a Network Performance 156 provides data regarding the performance of a network of healthcare providers and patients with respect to treatment plans, treatment regimens, and/or treatment goals in the form of data assessing metrics of performance of healthcare providers with respect to their patients. For example, when the third party use is a payer a metric provided in a Network Performance 156, in some embodiments, comprises a number of complications resulting from a particular treatment provided by a healthcare provider to his or her patients. For example, when the third party use is a payer, a metric provided in a Network Performance 156, in some embodiments, comprises a patient satisfaction score as generated by a data Insights Engine 100 as described herein. In some embodiments, Network Outcome data sub-grouping 158 comprises a portal dedicated to that grouping and, in some embodiments, comprises a portion of a portal shared with other data.

In some embodiments, a Network Outcomes 158 provides data regarding the performance of a network of healthcare providers and patients with respect to treatment plans, treatment regimens, and/or treatment goals. In some embodiments, a Network Outcomes 158 provides data to a third party relating to outcomes resulting from treatments provided by a healthcare provider to his or her patients. For example, when the third party use is a payer, a metric provided in a Network Outcome data sub-grouping 158, in some embodiments, comprises a survival rate for a particular diagnosis. For example, when the third party user is a payer, a metric provided in a Network Outcome data sub-grouping 158, in some embodiments, comprises a total cost of treatment. In some embodiments, a Data Insights Engine 100 provides analysis of outcomes of the one or more healthcare providers within the Network Outcome data sub-grouping 158 by, for example, comparing the outcomes of a particular healthcare provider to other similarly situated healthcare providers. In some embodiments, Network Outcome data sub-grouping 158 comprises a portal dedicated to that grouping and, in some embodiments, comprises a portion of a portal shared with other data.

In some embodiments, a Pathway Management data sub-grouping 160 provides data regarding one or more treatment plans, treatment regimens, and/or treatment goals with respect to how the one or more treatment plans, treatment regimens, and/or treatment goals or an aspect thereof were carried out. In some embodiments, Pathway Management 160 comprises a portal dedicated to that grouping and, in some embodiments, comprises a portion of a portal shared with other data.

Digital Processing Device

In some embodiments, the platforms and methods described herein include a digital processing device or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server Oracle® Solaris®, Windows-Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile OS, Linux®, and Palm WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, and/or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

Figure 7:
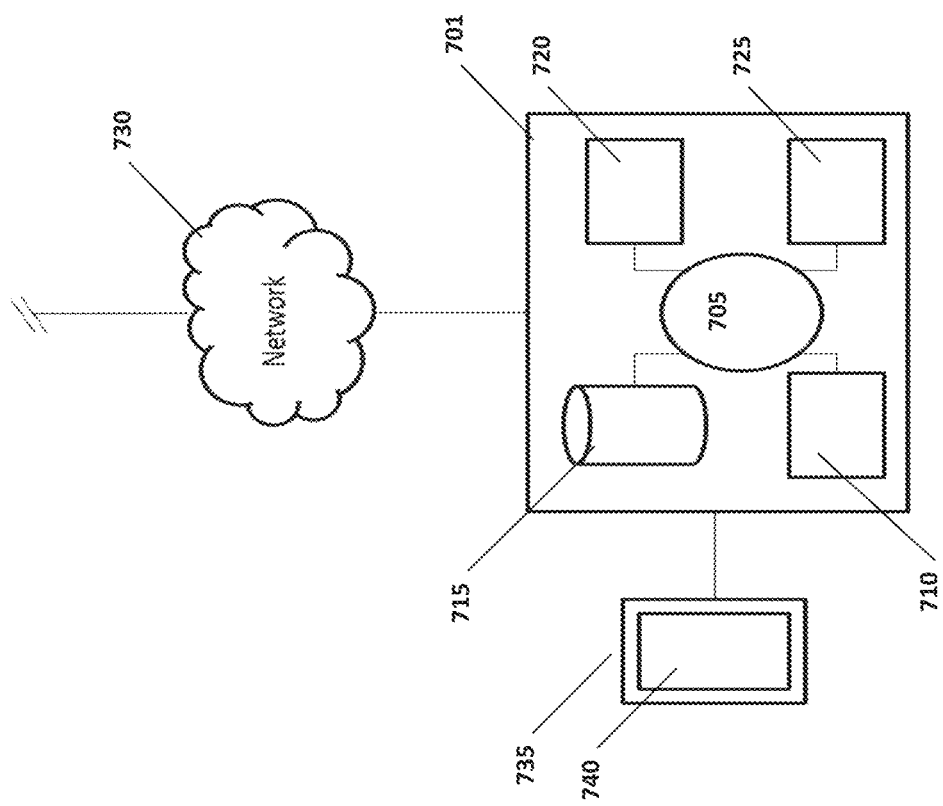
FIG. 7 shows an example of a digital processing device; in this case, a device with one or more CPUs, a memory, a communication interface, and a display.

FIG. 7 shows an exemplary digital processing device 701 programmed or otherwise configured to store profiles, ingest health data from external sources, value individual profiles, and/or provide interfaces for searching profiles. In this embodiment, the digital processing device 701 includes a central processing unit (CPU, also "processor" and "computer processor" herein) 705, which can be a single core or multi core processor, or a plurality of processors for parallel processing. The digital processing device 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The digital processing device 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 1530 can include one or more computer servers, which can enable distributed computing, such as cloud computing. The network 730, in some cases with the aid of the device 701, can implement a peer-to-peer network, which may enable devices coupled to the device 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and write back. The CPU 705 can be part of a circuit, such as an integrated circuit. One or more other components of the device 701 can be included in the circuit. In some cases, the circuit is an application specific integrated circuit (ASIC) or a field programmable gate array (FPGA).

The storage unit 715 can store files, such as drivers, libraries and saved programs. The storage unit 715 can store user data, e.g., user preferences and user programs. The digital processing device 701 in some cases can include one or more additional data storage units that are external, such as located on a remote server that is in communication through an intranet or the Internet.

The digital processing device 701 can communicate with one or more remote computer systems through the network 730. For instance, the device 701 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 701, such as, for example, on the memory 710 or electronic storage unit 715. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

Non-Transitory Computer Readable Storage Medium

In some embodiments, the platforms and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 8:
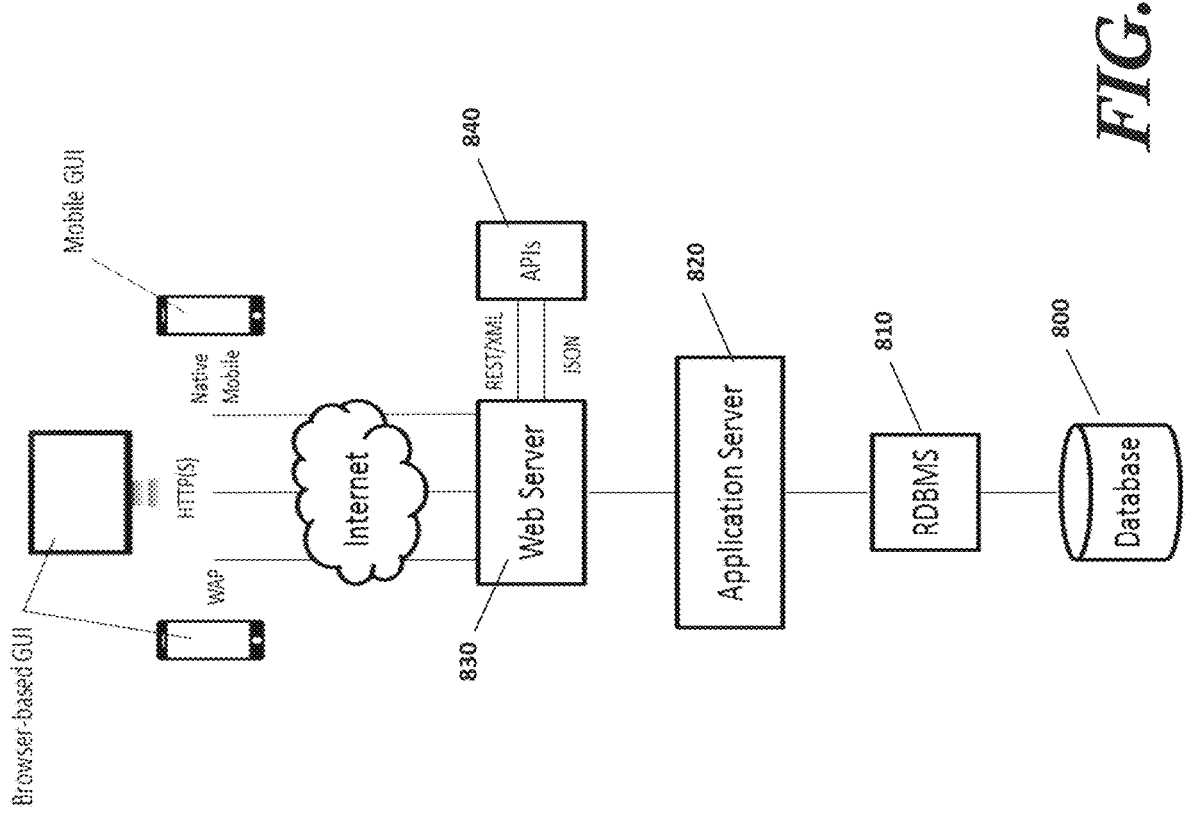
FIG. 8 shows an example of a web/mobile application provision system; in this case, a system providing browser-based and/or native mobile user interfaces.

FIG. 8 shows an exemplary application provision system which comprises one or more databases 800 accessed by a relational database management system (RDBMS) 810. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 820 (such as Java servers, .NET servers, PHP servers, and the like) and one or more web servers 830 (such as Apache, IIS, GWS and the like). The web server(s) optionally expose one or more web services via app application programming interfaces (APIs) 840. Via a network, such as the Internet, the system provides browser-based and/or mobile native user interfaces.

Figure 9:
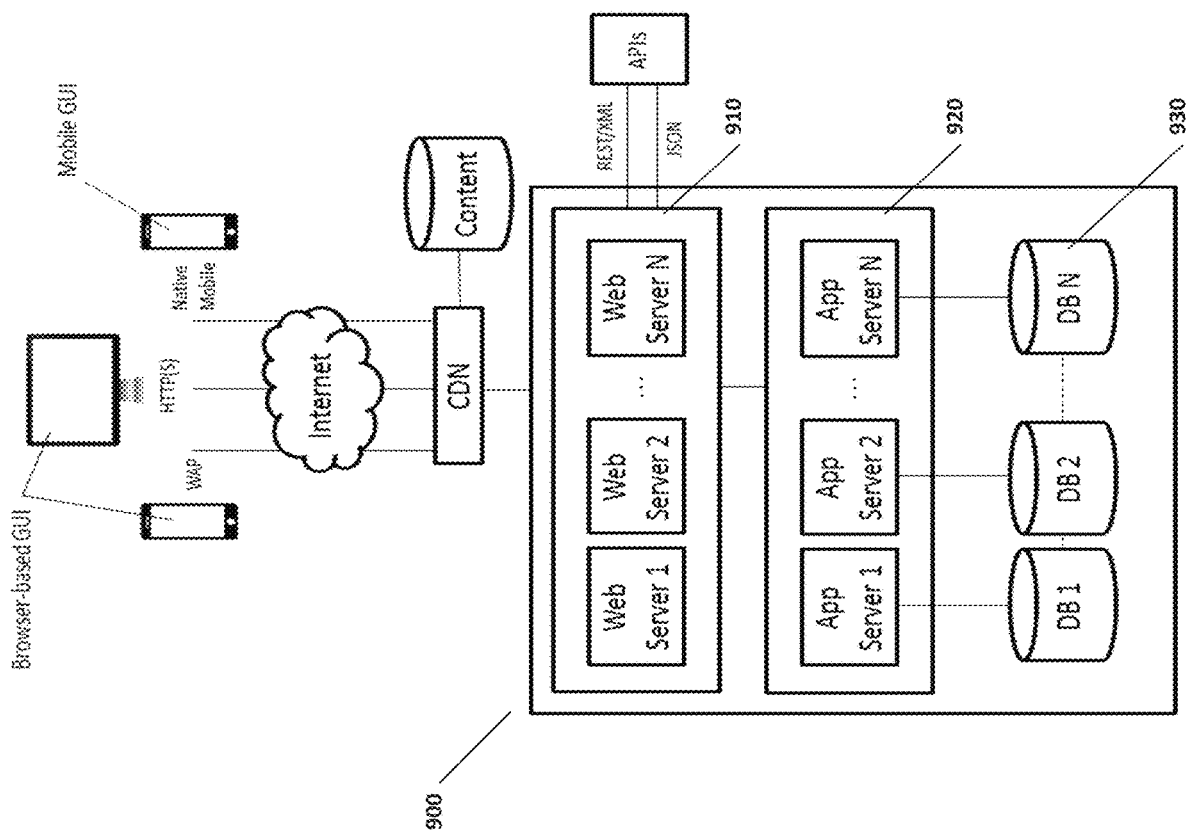
FIG. 9 shows an example of a cloud-based web/mobile application provision system; in this case, a system comprising an elastically load balanced, auto-scaling web server and application server resources as well synchronously replicated databases.

FIG. 9 shows an exemplary application provision system which alternatively has a distributed, cloud-based architecture 900 and comprises elastically load balanced, auto-scaling web server resources 910 and application server resources 920 as well synchronously replicated databases 930.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony PSP™ browser.

Software Modules

In some embodiments, the platforms and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of profile, fitness, genetic, health, profile value, and trust information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1—Lung Cancer Cohort Modeling

Figure 12:
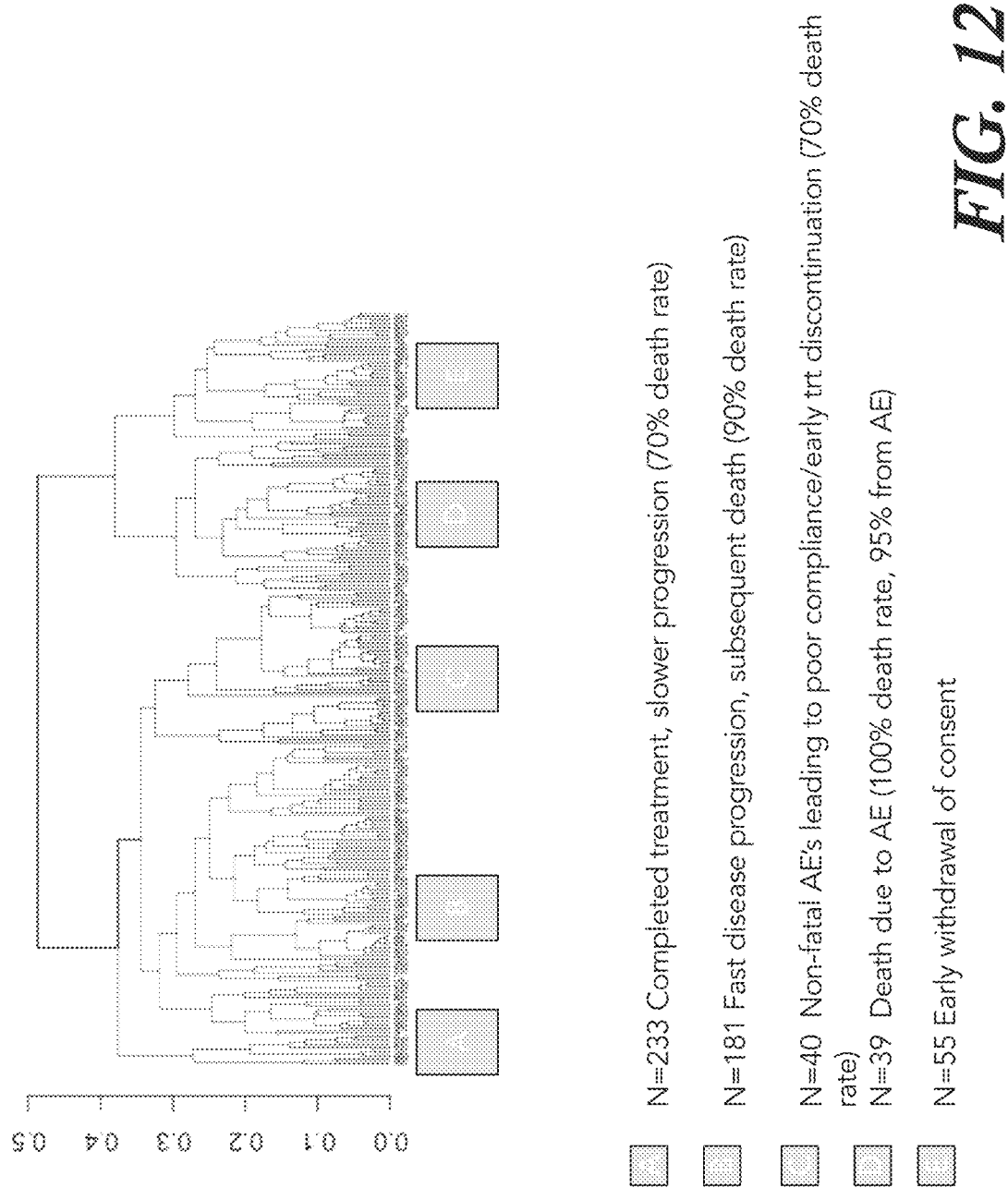
FIG. 12 shows the dendrogram output of a clustering algorithm identifying major multi-outcome patient cohorts.

Hierarchical clustering was carried out for a data set for lung cancer patients. The clustering algorithm identified five major multi-outcome patient cohorts as illustrated in FIG. 12. The five cohorts correspond to the following groups: (A) completed treatment, slower progression (70% death rate; n=233); (B) fast disease progression, subsequent death (90% death rate; n=181); (C) non-fatal adverse events leading to poor compliance/early TRT discontinuation (70% death rate; n=40); (D) death rate due to adverse event (100% death rate, 95% from adverse event; n=39); (E) early withdrawal of consent (n=55). The intercept represents a baseline probability before taking into account patient specific information.

Figure 13:
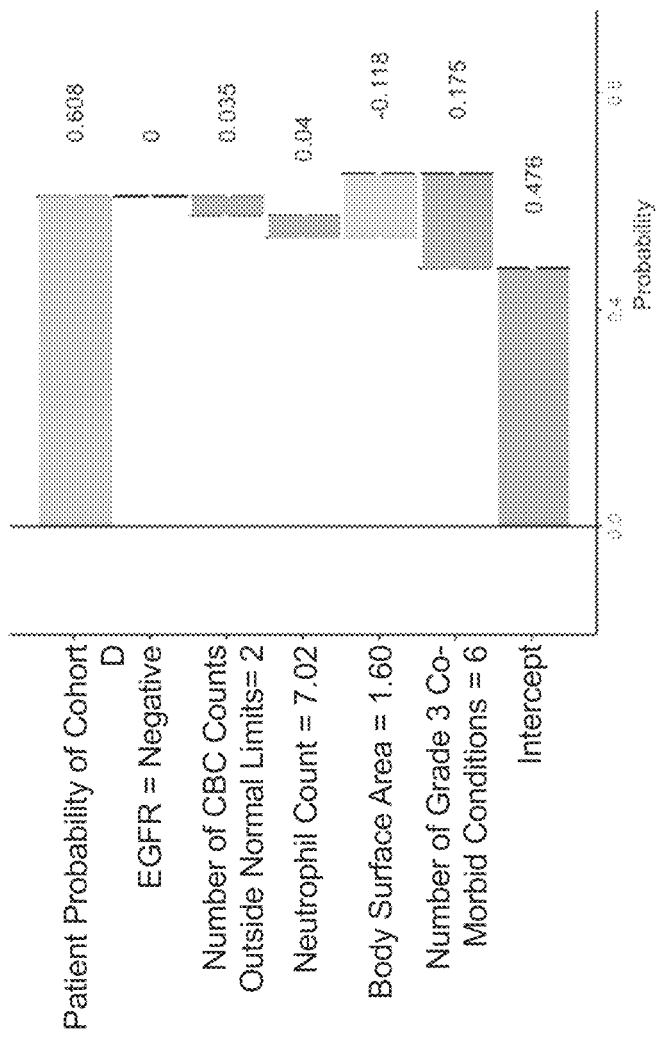
FIG. 13 shows an illustrative prediction for a particular multi-outcome cohort for an individual.

Next, a machine learning model was trained using data labeled with the five patient cohorts found in FIG. 12. The trained model was used to predict a probability of a patient being in a given cohort. FIG. 13 shows illustrative results for an individual with the top prediction for the patient being Cohort D (60.8% probability). The estimated contributions to this prediction by top predictive parameters are shown as well: EGFR negative, CBC counts outside of normal, neutrophil count, body surface area, and number of grade 3 co-morbid conditions.

Example 2—Adverse Event Data Visualization

Figure 14:
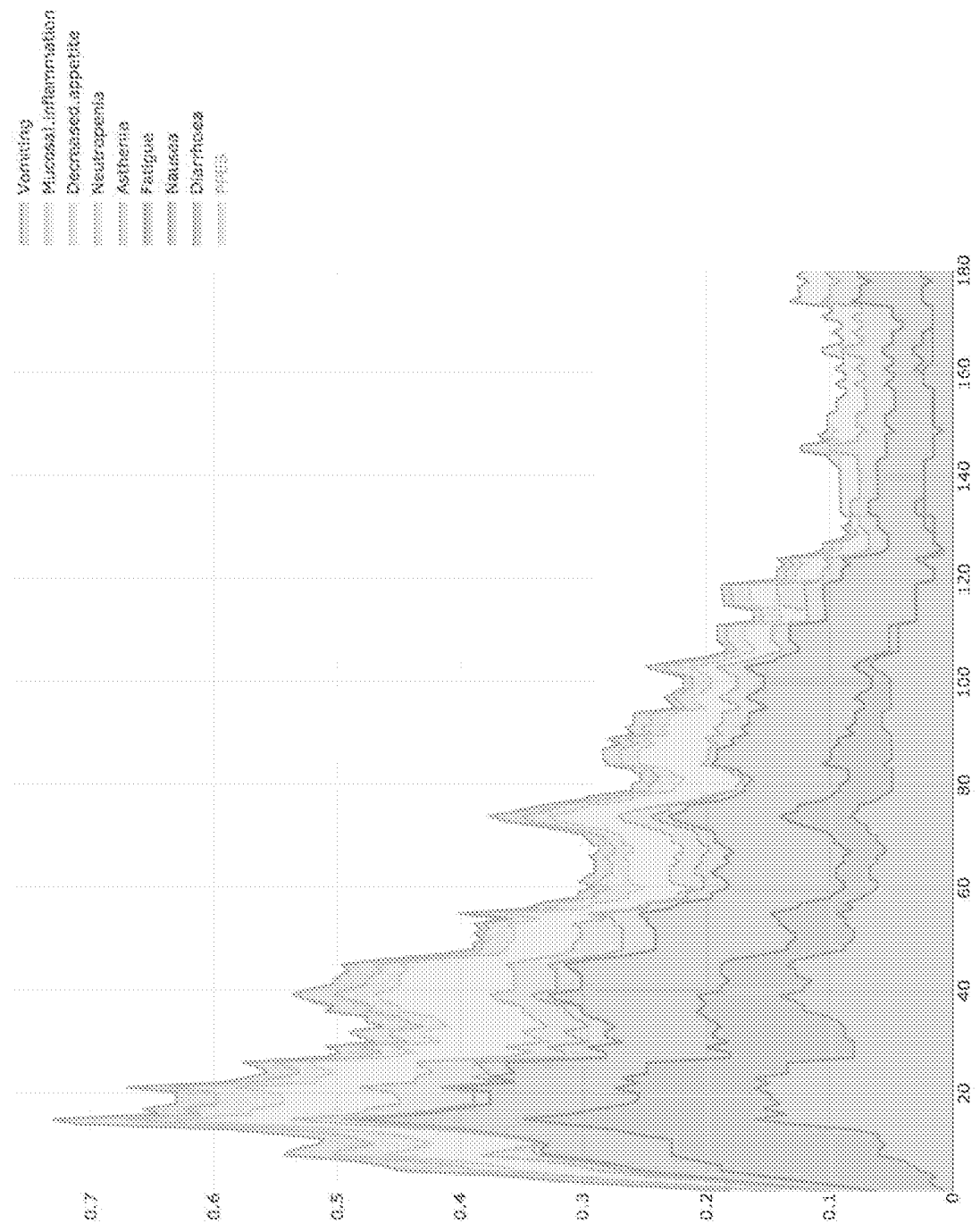
FIG. 14 shows a visual display of an adverse event model output with the adverse event (AE) burden distributed over time after the start of treatment.
Figure 15:
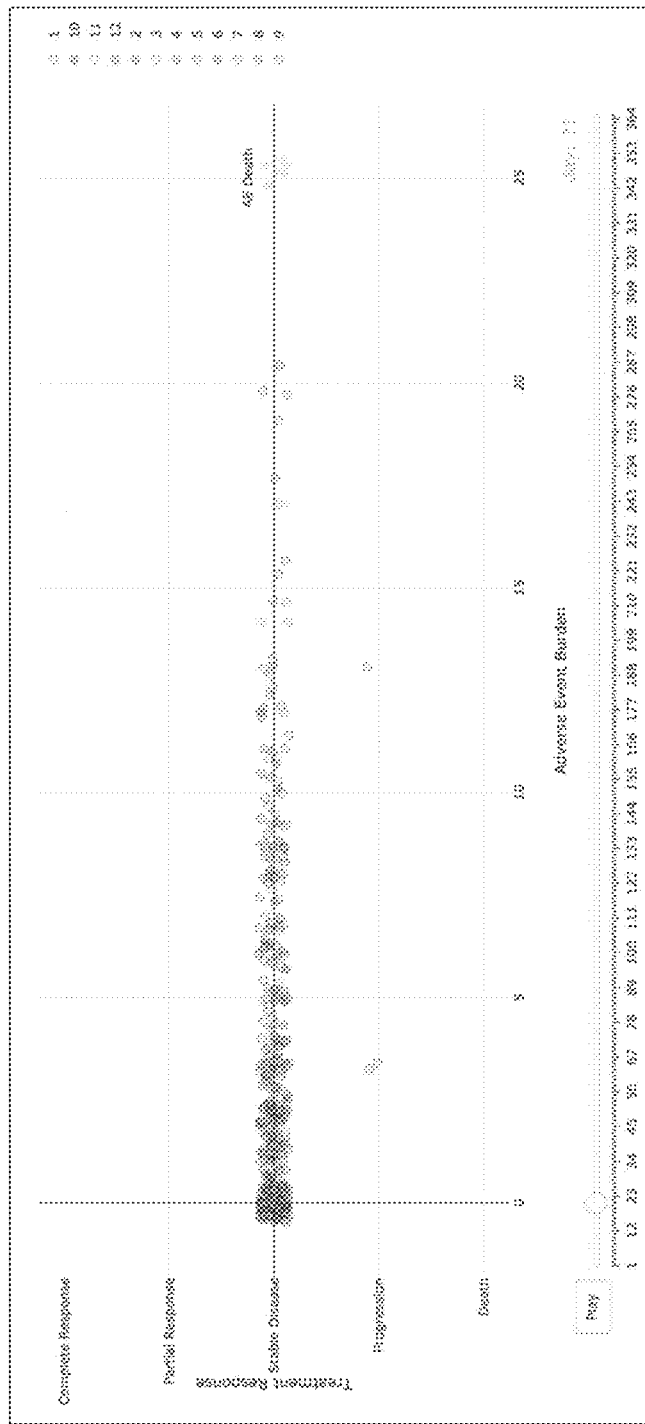
FIG. 15 shows a visual display of a model cohort output in which each patient is a point. The x-axis is the adverse event burden, and the y-axis is the treatment efficacy response.

A machine learning model is trained using a training data set labeled with adverse event outcomes to make predictions based on a single outcome (adverse events). FIG. 14 provides a visual display of the adverse event model output with the adverse event (AE) burden distributed over time on a daily basis after the start of treatment. The individual components to the AE burden (each type of adverse event) are shown in stacked curves. The visualization illustrates how the average adverse event burden is tends to occur early on during treatment, peaking around 3 weeks. FIG. 15 provides a visual display of the model cohort output. Each patient is a point. The x-axis is the adverse event burden, and the y-axis is the treatment efficacy response. The AE burden is computed by summing the individual adverse events while accounting for their magnitude (e.g., five mild AEs may add up to an AE burden of 5 while a single severe AE may provide a burden of 5). Pressing the "play" button/icon shows how the individual points are mapped onto the figure over time with the motion of the points showing their time course.

What is claimed is:

1. A computer-implemented method comprising:
 (a) receiving a data set comprising a plurality of features and outcome information corresponding to a plurality of patients;
 (b) applying a clustering algorithm to said outcome information corresponding to said plurality of patients to identify two or more clusters defined by a plurality of outcomes comprising at least one of disease survival, disease progression, treatment efficacy, or adverse event for a treatment, wherein said two or more clusters comprise a first multi-outcome cluster defined by a first combined set of outcomes and a second multi-outcome cluster defined by a second combined set of outcomes;
 (c) generating a predictive model using a machine learning algorithm, wherein said predictive model is configured to determine associations between said plurality of features within said data set and said two or more clusters defined by said plurality of outcomes;
 (d) evaluating an input data for a patient using said predictive model to generate an output comprising a determination of the first multi-outcome cluster or the second multi-outcome cluster selected from said two or more clusters, wherein said patient is predicted to have said first combined set of outcomes or said second combined set of outcomes based on said determination; and (e) providing a healthcare provider interface configured to present a visual representation of data from the first multi-outcome cluster or the second multi-outcome cluster determined for said patient, wherein said visual representation shows a cohort definition subgrouping comprising patients belonging to at least the first multi-outcome cluster or the second multi-outcome cluster.

2. The method of claim 1, further comprising converting said data set into a plurality of data points, each of said plurality of data points comprising parameters corresponding to said outcome information.

3. The method of claim 2, further comprising computing distances between each of said plurality of data points based on said parameters, thereby generating a distance matrix.

4. The method of claim 1, further comprising generating a dendrogram visually representing said two or more clusters.

5. The method of claim 1, wherein said clustering algorithm comprises K-means clustering, mean-shift clustering, or hierarchical clustering.

6. The method of claim 5, wherein said clustering algorithm is a hierarchical clustering algorithm.

7. The method of claim 1, wherein said predictive model comprises random forest, gradient boosted trees, recurrent neural networks, naïve bayes classifiers, or penalized multinomial regression.

8. The method of claim 1, wherein said data set comprises health data for said plurality of subjects retrieved from an electronic medical record.

9. The method of claim 8, further comprising processing said electronic medical record using a natural language processing algorithm to extract a plurality of features from said data set for training said predictive model.

10. The method of claim 8, wherein said natural language processing algorithm comprises one or more rules for keyword identification, unit conversion, internal consistency, or any combination thereof.

11. The method of claim 8, wherein said natural language processing algorithm comprises a natural language processing model configured to annotate said electronic medical record with gold standard labels.

12. The method of claim 8, wherein said natural language processing algorithm comprises generating rules based on raw data from the electronic medical record, and then using the rules to train a model to apply to said raw data to standardize said electronic medical record.

13. The method of claim 8, further comprising generating one or more insights to assist in providing guidance for a treatment, wherein said one or more insights is based on said output comprising said determination of the first multi-outcome cluster or the second multi-outcome cluster selected from said two or more clusters.

14. The method of claim 13, further comprising providing a healthcare provider application comprising a healthcare provider interface configured to present a healthcare provider with said one or more insights comprising said guidance regarding said treatment and a patient application comprising a patient interface configured to receive said input data for said patient.

15. The method of claim 14, wherein said healthcare provider interface comprises a first plurality of portals, wherein at least one of said first plurality of portals comprises a patient context data grouping comprising said health data.

16. The method of claim 15, wherein at least one of said first plurality of portals comprises an outcomes navigator data grouping comprising said outcome information.

17. The method of claim 15, wherein said patient context data grouping comprises a second plurality of portals comprising an interactive timeline of a disease of said patient, interactive radiology imaging of said patient, a medical history of said patient and a current status of said patient, or any combination thereof.

18. The method of claim 14, wherein said two or more clusters are based on said outcome information comprising one or more of progression, adverse event status, treatment status, or mortality.

19. The method of claim 18, wherein said predictive model comprises a plurality of features comprising one or more of: (1) age, (2) gender, (3) race, (4) exposure, (5) co-morbidity, (6) diagnosis, (7) prognosis, (8) tumor pathology, (9) serum markers, (10) radiology findings, (11) family history, (12) surgical history, (13) treatment plan, (14) treatment regimen, or (15) treatment goal.

20. The method of claim 14, further comprising selecting published data that is most relevant to said patient and presenting said published data within said healthcare provider interface, wherein said healthcare provider interface comprises a portal that is configured to present said published data relating to said patient.

21. The method of claim 14, wherein said healthcare provider interface comprises a portal that comprises a comparison of a performance of said healthcare provider to a performance of other healthcare providers.

22. The method of claim 1, wherein said plurality of outcomes comprises cancer survival, cancer progression, adverse event for a treatment, or any combination thereof.

23. The method of claim 22, wherein said adverse event comprises neutropenia, leucopenia, thrombocytopenia, fatigue, pain, mucositis, skin rash, nausea, vomiting, constipation, diarrhea, cognitive dysfunction, nerve damage, appetite loss, organ damage, or any combination thereof.

24. The method of claim 1, further comprising generating one or more single-outcome predictive models using a second machine learning algorithm, and evaluating said input data for said patient using said one or more single-outcome predictive models to generate a single output comprising a single predicted outcome.

25. The method of claim 24, wherein said one or more single-outcome predictive models comprise random forest, gradient boosted trees, penalized linear regression, penalized logistic regression, cox regression, naïve bayes classifiers, support vector machines, or recurrent neural network.

26. The method of claim 1, wherein the visual representation comprising the cohort definition subgrouping displays a timeline of one or more interconnected treatment pathways for the cohort definition subgrouping in an interactive visual format.

27. The method of claim 26, wherein the healthcare provider interface provides selectable options for one or more of showing treatment pathways, regimen comparisons, and algorithms and/or guidelines.

28. The method of claim 26, wherein the healthcare provider interface further comprises a treatment explorer showing disease progression over time for at least one similarly situated person belonging to at least the first multi-outcome cluster or the second multi-outcome cluster.

29. A computer-implemented system comprising:
(a) one or more processors;
(b) a non-transitory computer readable storage medium encoded with a computer program that causes the one or more processors to:
 (i) receive a data set comprising a plurality of features and outcome information corresponding to a plurality of patients;
 (ii) apply a clustering algorithm to said outcome information corresponding to said plurality of patients to identify two or more clusters defined by a plurality of outcomes comprising at least one of disease survival, disease progression, treatment efficacy, or adverse event for a treatment, wherein said two or more clusters comprise a first multi-outcome cluster defined by a first combined set of outcomes and a second multi-outcome cluster defined by a second combined set of outcomes;
 (iii) generate a predictive model using a machine learning algorithm, wherein said predictive model is configured to determine associations between said plurality of features within said data set and said two or more clusters defined by said plurality of outcomes;
 (iv) evaluate an input data for a patient using said predictive model to generate an output comprising a determination of the first multi-outcome cluster or the second multi-outcome cluster selected from said two or more clusters, wherein said patient is predicted to have said first combined set of outcomes or said second combined set of outcomes based on said determination; and
 (v) provide a healthcare provider interface configured to present a visual representation of data from the first multi-outcome cluster or the second multi-outcome cluster determined for said patient, wherein said visual representation shows a cohort definition subgrouping comprising patients belonging to at least the first multi-outcome cluster or the second multi-outcome cluster.

30. A computer-implemented method comprising:
receiving a data set comprising a plurality of features and outcome information corresponding to a plurality of patients;
applying a clustering algorithm to said outcome information corresponding to said plurality of patients to identify two or more clusters defined by a plurality of outcomes comprising at least one of disease survival, disease progression, treatment efficacy, or adverse event for a treatment, wherein said two or more clusters comprise a first multi-outcome cluster defined by a first combined set of outcomes and a second multi-outcome cluster defined by a second combined set of outcomes;
generating a predictive model using a machine learning algorithm that determines associations between said plurality of features within said data set and said two or more clusters defined by said plurality of outcomes such that the predictive model is configured to evaluate an input data for a patient and generate an output comprising a determination of the first multi-outcome cluster or the second multi-outcome cluster selected from said two or more clusters, wherein said patient is predicted to have said first combined set of outcomes or said second combined set of outcomes based on said determination; and
provide a healthcare provider interface configured to present a visual representation of data from the first multi-outcome cluster or the second multi-outcome cluster determined for said patient, wherein said visual representation shows a cohort definition subgrouping comprising patients belonging to at least the first multi-outcome cluster or the second multi-outcome cluster.

\* \* \* \* \*